(12) United States Patent
Georgescu et al.

(10) Patent No.: US 10,643,105 B2
(45) Date of Patent: May 5, 2020

(54) INTELLIGENT MULTI-SCALE MEDICAL IMAGE LANDMARK DETECTION

(71) Applicant: Siemens Healthcare GmbH, Erlangen (DE)

(72) Inventors: Bogdan Georgescu, Plainsboro, NJ (US); Florin Cristian Ghesu, Erlangen (DE); Yefeng Zheng, Princeton Junction, NJ (US); Dominik Neumann, Erlangen (DE); Tommaso Mansi, Plainsboro, NJ (US); Dorin Comaniciu, Princeton Junction, NJ (US); Wen Liu, San Jose, CA (US); Shaohua Kevin Zhou, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 4 days.

(21) Appl. No.: 15/689,411

(22) Filed: Aug. 29, 2017

(65) Prior Publication Data
US 2018/0005083 A1 Jan. 4, 2018

Related U.S. Application Data
(63) Continuation of application No. 15/397,638, filed on Jan. 3, 2017, now Pat. No. 9,792,531, which is a
(Continued)

(51) Int. Cl.
*G06K 9/62* (2006.01)
*G06N 3/08* (2006.01)
(Continued)

(52) U.S. Cl.
CPC ......... *G06K 9/6256* (2013.01); *A61B 5/0044* (2013.01); *A61B 5/055* (2013.01); *A61B 6/032* (2013.01); *A61B 6/5217* (2013.01); *A61B 8/0883* (2013.01); *A61B 8/4416* (2013.01); *A61B 8/483* (2013.01); *A61B 8/5223* (2013.01); *G06K 9/2063* (2013.01); *G06K 9/2081* (2013.01); *G06K 9/4628* (2013.01); *G06K 9/627* (2013.01); *G06K 9/6267* (2013.01); *G06K 9/66* (2013.01); *G06N 3/006* (2013.01);
(Continued)

(58) Field of Classification Search
CPC .......... G06K 9/00718; G06K 9/00302; G06K 9/00335; G06K 9/00456; G06K 9/6219
See application file for complete search history.

(56) References Cited

PUBLICATIONS

Zheng et al: "Four-Chamber Heart Modeling and Automatic Segmentation for 3-D Cardiac CT Volumes Using Marginal Space Learning and Steerable Features", IEEE, 2008. (Year: 2008).*
(Continued)

*Primary Examiner* — Ruiping Li

(57) ABSTRACT

Intelligent multi-scale image parsing determines the optimal size of each observation by an artificial agent at a given point in time while searching for the anatomical landmark. The artificial agent begins searching image data with a coarse field-of-view and iteratively decreases the field-of-view to locate the anatomical landmark. After searching at a coarse field-of view, the artificial agent increases resolution to a finer field-of-view to analyze context and appearance factors to converge on the anatomical landmark. The artificial agent determines applicable context and appearance factors at each effective scale.

19 Claims, 28 Drawing Sheets

Related U.S. Application Data continuation-in-part of application No. 15/160,699, filed on May 20, 2016, now Pat. No. 9,569,736.

(60) Provisional application No. 62/396,480, filed on Sep. 19, 2016, provisional application No. 62/254,601, filed on Nov. 12, 2015, provisional application No. 62/219,432, filed on Sep. 16, 2015.

(51) Int. Cl.

| | | |
|---|---|---|
| *G06T 7/00* | (2017.01) | |
| *G06K 9/20* | (2006.01) | |
| *G06K 9/66* | (2006.01) | |
| *G06T 7/70* | (2017.01) | |
| *A61B 8/08* | (2006.01) | |
| *A61B 5/055* | (2006.01) | |
| *A61B 5/00* | (2006.01) | |
| *A61B 8/00* | (2006.01) | |
| *A61B 6/00* | (2006.01) | |
| *G06K 9/46* | (2006.01) | |
| *G16H 50/20* | (2018.01) | |
| *A61B 6/03* | (2006.01) | |
| *G06T 7/73* | (2017.01) | |
| *G16H 50/70* | (2018.01) | |
| *G16H 30/40* | (2018.01) | |
| *G06N 3/00* | (2006.01) | |
| *G06N 7/00* | (2006.01) | |
| *G06F 19/00* | (2018.01) | |

(52) U.S. Cl.
CPC .............. *G06N 3/08* (2013.01); *G06N 7/005* (2013.01); *G06T 7/0012* (2013.01); *G06T 7/70* (2017.01); *G06T 7/73* (2017.01); *G16H 30/40* (2018.01); *G16H 50/20* (2018.01); *G16H 50/70* (2018.01); *G06F 19/321* (2013.01); *G06K 2209/051* (2013.01); *G06N 3/084* (2013.01); *G06T 2207/10016* (2013.01); *G06T 2207/10088* (2013.01); *G06T 2207/20016* (2013.01); *G06T 2207/20081* (2013.01); *G06T 2207/30048* (2013.01); *G06T 2207/30204* (2013.01)

(56) References Cited

PUBLICATIONS

Wang et al: "A General Framework for Context-Specific Image segmentation using reinforcement learning", IEEE, 2013. (Year: 2013).*

Appel, Kenneth, and Wolfgang Haken. "Every planar map is four colorable. Part I: Discharging." Illinois Journal of Mathematics 21.3 (1977): 429-490.

Bellemare, Marc G., et al. "The arcade learning environment: An evaluation platform for general agents." Journal of Artificial Intelligence Research (2012).

Bellman, Richard. "The theory of dynamic programming" No. RAND-P-550. RAND Corp Santa Monica CA, 1954.

Bengio, Yoshua, Aaron C. Courville, and Pascal Vincent. "Unsupervised feature learning and deep learning: A review and new perspectives." CoRR, abs/1206.5538 1 (2012).

Bengio, Yoshua, Aaron Courville, and Pierre Vincent. "Representation learning: A review and new perspectives." Pattern Analysis and Machine Intelligence, IEEE Transactions on 35.8 (2013): 1798-1828.

Boser, Bernhard E., Isabelle M. Guyon, and Vladimir N. Vapnik. "A training algorithm for optimal margin classifiers." Proceedings of the fifth annual workshop on Computational learning theory. ACM, 1992.

Breiman, Leo. "Random forests." Machine learning 45.1 (2001): 5-32.

Caicedo, Juan C., and Svetlana Lazebnik. "Active object localization with deep reinforcement learning." Proceedings of the IEEE International Conference on Computer Vision. 2015.

Ciresan, Dan, et al. "Deep neural networks segment neuronal membranes in electron microscopy images." Advances in neural information processing systems. 2012.

Ciresan, Dan, Ueli Meier, and Jürgen Schmidhuber. "Multi-column deep neural networks for image classification." Computer Vision and Pattern Recognition (CVPR), 2012 IEEE Conference on. IEEE, 2012.

Ghesu, Florin C., et al. "Marginal Space Deep Learning: Efficient Architecture for Detection in Volumetric Image Data." Medical Image Computing and Computer-Assisted Intervention—MICCAI 2015. Springer International Publishing, 2015. 710-718.

Graves, Alan, Abdel-rahman Mohamed, and Geoffrey Hinton. "Speech recognition with deep recurrent neural networks" Acoustics, Speech and Signal Processing (ICASSP), 2013 IEEE International Conference on. IEEE, 2013.

Heess, Nicolas, David Silver, and Yee Whye Teh. "Actor-Critic Reinforcement Learning with Energy-Based Policies." EWRL. 2012.

Hinton, Geoffrey E., Simon Osindero, and Yee-Whye Teh. "A fast learning algorithm for deep belief nets." Neural computation 18.7 (2006): 1527-1554.

Hubel, D. H., and T. N. Wiesel. "Shape and arrangement of columns in cat's striate cortex." The Journal of physiology 165.3 (1963): 559.

Krizhevsky, Alex, Ilya Sutskever, and Geoffrey E. Hinton. "Imagenet classification with deep convolutional neural networks." Advances in neural information processing systems. 2012.

Lange, Sascha, and Martin Riedmiller. "Deep auto-encoder neural networks in reinforcement learning." Neural Networks (IJCNN), The 2010 International Joint Conference on. IEEE, 2010.

LeCun, Yann, et al. "Gradient-based learning applied to document recognition." Proceedings of the IEEE 86.11 (1998): 2278-2324.

Lin, Long-Ji. "Reinforcement learning for robots using neural networks" No. CMU-CS-93-103. Carnegie-Mellon Univ Pittsburgh PA School of Computer Science, 1993.

Lu, Xiaoguang, and Marie-Pierre Jolly. "Discriminative context modeling using auxiliary markers for LV landmark detection from a single MR image." Statistical Atlases and Computational Models of the Heart. Imaging and Modelling Challenges. Springer Berlin Heidelberg, 2012. 105-114.

Lu, Xiaoguang, et al. "Cardiac anchoring in MRI through context modeling." International Conference on Medical Image Computing and Computer-Assisted Intervention. Springer Berlin Heidelberg, 2010.

Mnih, Volodymyr, et al. "Human-level control through deep reinforcement learning." Nature 518.7540 (2015): 529-533.

Nair, Vinod, and Geoffrey E. Hinton. "Rectified linear units improve restricted boltzmann machines." Proceedings of the 27th International Conference on Machine Learning (ICML-10). 2010.

Neumann, Dominik, et al. "Vito—A Generic Agent for Multi-physics Model Personalization: Application to Heart Modeling." Medical Image Computing and Computer-Assisted Intervention—MICCAI 2015. Springer International Publishing, 2015. 442-449.

Park, Hee-Jun, Byung Kook Kim, and Kye Young Lim. "Measuring the machine intelligence quotient (MIQ) of human-machine cooperative systems." Systems, Man and Cybernetics, Part A: Systems and Humans, IEEE Transactions on 31.2 (2001): 89-96.

Riedmiller, Martin. "Neural fitted Q iteration—first experiences with a data efficient neural reinforcement learning method." Machine Learning: ECML 2005. Springer Berlin Heidelberg, 2005. 317-328.

Rogers, Timothy T., and James L. McClelland. "Parallel distributed processing at 25: Further explorations in the microstructure of cognition." Cognitive science 38.6 (2014): 1024-1077.

Russell, Stuart, Peter Norvig, and Artificial Intelligence. "A modern approach." Artificial Intelligence. Prentice-Hall, Egnlewood Cliffs 25 (1995).

Sallans, Brian, and Geoffrey E. Hinton. "Reinforcement learning with factored states and actions." The Journal of Machine Learning Research 5 (2004): 1063-1088.

(56) References Cited

PUBLICATIONS

Sawada, Yoshihide, and Kazuki Kozuka. "Transfer learning method using multi-prediction deep Boltzmann machines for a small scale dataset." Machine Vision Applications (MVA), 2015 14th IAPR International Conference on. IEEE, 2015.

Sermanet, Pierre, et al. "Overfeat: Integrated recognition, localization and detection using convolutional networks." arXiv preprint arXiv:1312.6229 (2013).

Smolensky, Paul. "Information Processing in Dynamical Systems: Foundations of Harmony Theory; CU-CS-321-86." (1986).

Sutton, Richard S., and Andrew G. Barto. Introduction to reinforcement learning. vol. 135. Cambridge: MIT Press, 1998.

Sutton, Richard S., and Andrew G. Barto. Reinforcement learning: An introduction. MIT press, 1998.

Tsitsiklis, John N., and Benjamin Van Roy. "An analysis of temporal-difference learning with function approximation." Automatic Control, IEEE Transactions on 42.5 (1997): 674-690.

Tu, Zhuowen. "Probabilistic boosting-tree: Learning discriminative models for classification, recognition, and clustering." Computer Vision, 2005. ICCV 2005. Tenth IEEE International Conference on. vol. 2. IEEE, 2005.

Turing, Alan M. "Computing machinery and intelligence." Mind 59.236 (1950): 433-460.

Vincent, Pascal, et al. "Stacked denoising autoencoders: Learning useful representations in a deep network with a local denoising criterion." The Journal of Machine Learning Research 11 (2010): 3371-3408.

Watkins, Christopher JCH, and Peter Dayan. "Q-learning." Machine learning 8.3-4 (1992): 279-292.

Zheng, Yefeng, et al. "3D deep learning for efficient and robust landmark detection in volumetric data." International Conference on Medical Image Computing and Computer-Assisted Intervention. Springer International Publishing, 2015.

Zheng, Yefeng, et al. "Four-chamber heart modeling and automatic segmentation for 3-D cardiac CT volumes using marginal space learning and steerable features." Medical Imaging, IEEE Transactions on 27.11 (2008): 1668-1681.

Wang, Lichao; et al; "A general framework for context-specific images segmentation using reinforcement learning";IEEE Transactions on medical imaging, vol. 32,No. 5;May 2003; pp. 943-956.

\* cited by examiner

500

510

520

700

710

720

INTELLIGENT MULTI-SCALE MEDICAL IMAGE LANDMARK DETECTION

CROSS-REFERENCE TO RELATED APPLICATIONS

This application is a continuation under 37 C.F.R. § 1.53(b) and 35 U.S.C. § 120 of U.S. patent application Ser. No. 15/397,638, filed Jan. 3, 2017, which claims the benefit of the filing date under 35 U.S.C. § 119(e) of U.S. Provisional Application No. 62/396,480, filed Sep. 19, 2016 and which is a continuation-in-part under 37 C.F.R. § 1.53(b) and 35 U.S.C. § 120 of U.S. patent application Ser. No. 15/160,699, filed May 20, 2016, which claims the benefit of the filing date under 35 U.S.C. § 119(e) of U.S. Provisional Application No. 62/219,432, filed Sep. 16, 2015, and U.S. Provisional Application No. 62/254,601, which are hereby incorporated by reference in their entirety.

FIELD

The disclosure is generally directed to medical image landmark detection, and more particularly, to machine learning for multi-scale navigation of image parsing with deep reinforcement learning.

DESCRIPTION OF RELATED ART

Knowledge-driven computational models are at the core of machine learning. As known in the conventional art, knowledge-driven computational models provide automation of image processing emulating intelligence and learning from a human perspective. In general, intelligent behavior is viewed as the ability of a computer, an individual, or artificial entity to explore, learn, and understand tasks, as opposed to mechanically following pre-defined steps.

Automation of image processing transcends the speed and capabilities of image analysis performed by a person. Machine learning techniques based on prediction, classification, and recognition using data-driven learning algorithms expand the capabilities of computers and artificial entities beyond the repeated, mechanical execution of a set of pre-defined steps. Known machine learning methods follow pre-defined steps such as sequentially and exhaustively scanning for feature extraction within medical images from patients, even after a classifier has been trained to recognize features. For example, three-dimensional landmark detection is based on machine learning combined with exhaustive hypothesis scanning. An appearance model may be learned as a patch-wise classifier, such as a Probabilistic Boosting Tree or Deep Convolutional Neural Network, and the appearance model is then used to scan the three-dimensional parametric space to find the landmark location.

Conventional methods of machine learning-based medical image parsing focus on generating rigid classifiers trained using observation anchored in a parametric space to learn appearance models. A classifier learns its appearance models through training, that applies rigid sets of pre-defined steps. In training, the classifier analyzes given data examples based on handcrafted features. That is, method-related meta-parameters (e.g., regularization weights, ranges, scales) are hand-picked or tuned according to application-specific criteria. Parameter optimization is limited due to the general use of handcrafted features. Weak generalization is due to overfitting. An operator, engineer, or medical professional is required to understand the variability of the desired medical imaging analysis and identify a suitable model or set of meta-parameters to reach optimal performances. The computer then blindly executes its task to automate the medical imaging analysis.

Machine learning techniques for quickly identifying anatomy in medical images include Marginal Space Learning (MSL), deep learning such as Marginal Space Deep Learning (MSDL), Marginal Space Deep Regression (MSDR) and Approximated Marginal Space Deep Learning (AMSD). These machine learning techniques each employ efficient machine learning frameworks to analyze large medical image databases to determine relevant image features. Classifiers are trained to identify the learned relevant image features generated from the input space parameters. Accordingly, in order to create efficient computerized medical image analysis, classifiers and machine learning frameworks are individually customized to a specific medical image analysis task. Separate solutions must also be hand crafted to perform a medical image analysis task specific to the imaging modality of the acquired image data.

BRIEF SUMMARY

Improvements may be made in machine learning techniques, such as techniques for automated landmark detection in medical imaging. Systems, methods, and non-transitory computer readable medium are provided for generating, training, and deploying an artificial agent for intelligent landmark identification in images, including medical images of a patient. The disclosed system constructs an agent that both learns how to identify the location of an anatomical landmark in a set of image data and how to generate its own model of the task to perform by automatically determining an optimal policy for conducting image evaluation and identify one or several anatomical landmarks.

Additional Improvements to machine learning techniques include techniques directed to three-dimensional multi-scale landmark detection in medical imaging. In training a search strategy model for the task of multi-scale landmark detection, an artificial agent learns to navigate different resolutions to better learn to identify the location of a landmark. For example, a search window of varying size and resolution with respect to the landmark is used, defined by a scale-space of the image data, to expedite landmark detection and to increase the propensity of convergence on a target location. Using the scale-space, the agent searches the image data for the landmark at different scales, starting at a coarse scale and converging on the landmark location at a fine scale, improving the effectiveness and efficiency of the search. Therefore, in addition to learning optimal anatomical navigation-paths through parametric-space of image data, the agent also learns optimal multi-scale navigation through the scale-space of the image data. Thus, navigation of both the parametric-space and the scale-space of image data is provided. As such, the artificial agent is trained not only to distinguish the target anatomical object from the rest of the body but also how to find the object by learning and following an optimal navigation path to the target object in the image space.

A method for intelligent multi-scale image parsing is provided. The method includes specifying a state space of an artificial agent for discrete portions of a training image, with the state space specified by a parametric space and a scale space for the discrete portions of the training image. A set of actions is also determined, the set of actions including parametric actions specifying a possible change in the parametric space with respect to the training image and scale actions specifying a possible change in the scale space with respect to the training image. A reward system is established based on applying each action of the set of actions and is based on at least one target location of the training image. An optimal action-value function approximator is learned by the artificial agent specifying the behavior of the artificial agent to maximize a cumulative future reward value of the reward system. The behavior of the artificial agent is a sequence of actions moving the agent towards the at least one target location of the training image, and the sequence of actions includes at least one scale action.

A method of machine learning for intelligent multi-scale image parsing is also provided. The method includes receiving a plurality of training images and training an artificial agent to parse a test image to identify a landmark location in the test image based on the plurality of training images. Training the artificial agent simultaneously trains a search strategy model to search for the landmark location by parsing the test image by performing a series of actions including changing the position and the scale of a patch of the test image, and an appearance model to identify the landmark location in the patch of the test image. Parsing the test image searches less than the entire test image.

A method for intelligent multi-scale landmark identification in an image is provided. The method includes receiving image data representing the image and automatically parsing, by a learned artificial agent that includes an optimal action-value function, the received image data to identify a landmark location in the image. The learned artificial agent is configured to parameterize a patch of the image data in a trained hierarchical data representation. The hierarchical data representation is trained by maximizing a future reward of a reward system of the action-value function for each a plurality of available actions to reposition the patch of the image. The learned artificial agent is also configured to determine a sequence of actions from the plurality of available actions to reposition and rescale the patch based on the parameterized patch of the image data, and to identify the landmark location in the repositioned and rescaled patch of the image.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

Exemplary embodiments of the disclosure are described with reference to the following drawings.

DETAILED DESCRIPTION

Figure 1:
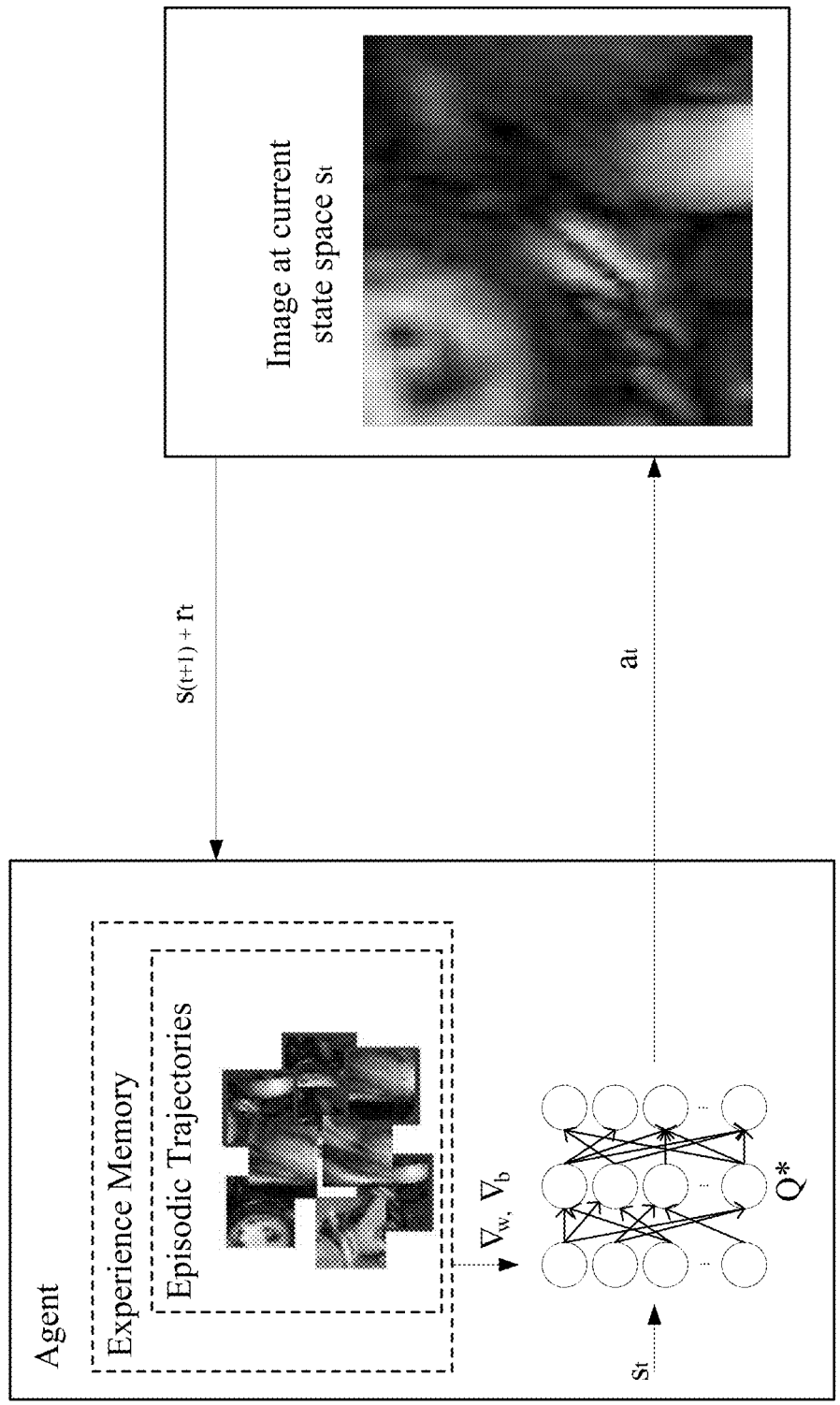
FIG. 1 illustrates a system in embodiment for generating and/or training and artificial agent for intelligent image parsing for medical imaging.

The conventional art fails to provide systems and methods that can understand the given problem by extracting knowledge and applying reasoning to generate a solution. The structure, training, and application of the conventional classifier does not permit the incorporation or discovery of intrinsic knowledge associated with the task execution, itself. Conventional solutions based on the handcrafted model are completely decoupled from this higher level of understanding, capable only of blindly executing the solution. The manual customization of the parameterized search sequence, rigidity in the order of applying classifiers, and/or manual pre-determination of specific dependent parameters distributions in the conventional machine learning techniques are difficult to scale to a large number of objects. The sequential and exhaustive scanning is repeated uniformly for each image scan based on a pre-defined set of scanning instructions, whereas the disclosed embodiments do not require such input. The artificial agents of the disclosed embodiments may be said to develop a set of scanning instructions, essentially "learning" to scan.

Fast and robust medical detection of anatomical structures, anatomical landmarks, and/or anatomical anomalies is beneficial to medical image analysis, enabling real-time guidance, quantification, and processing for diagnosis in the operating room. Machine learning methods may leverage large image databases to learn appearance models that capture variability in the image data. Conventional machine learning-based medical image landmark detection is limited to learning an appearance model and exhaustively scanning the space of parameters to find the optimum point, yielding suboptimal and unconstrained solutions. Feature computation and estimation of any other meta-parameters related to the appearance model or the search strategy of the conventional art are performed based on local criteria or predefined heuristics, leading to the rigid application of a specific search strategy applicable to a highly specialized task. Exhaustive search schemes are limited in meeting the accuracy requirements and computational efficiency needed during medical interventions.

A goal of some of the present embodiments is to address limitations of the conventional art in medical image analysis by simultaneously automating the modeling of both object appearance and the parameter search strategy as a unified behavioral task via an artificial agent. The disclosed embodiments achieve both the advantages of optimizing the execution of behavior learning through reinforcement learning with effective hierarchical feature extraction through deep learning. That is, given only a sequence of annotated images, the agent automatically learns strategies to localize image landmarks at a high accuracy. A further goal of the disclosed embodiments is to create a robust solution facilitating evaluation of images obtained by a variety of different medical imaging devices while achieving average detection errors of less than one to two pixels. A further goal is to automatically determine when an anatomical landmark is not contained within a medical image obtained from a patient. The disclosed embodiments advantageously create machine-driven image understanding in the context of medical image parsing. Physicians may benefit from the accurate, precise, specific, and/or sensitive detection in a medical image, aiding diagnosis using medical imaging technology.

An additional goal of some of the present embodiments is to improve automatically modeling both object appearance and the parameter search strategy as a unified behavioral task using an artificial agent and by providing a scaled search strategy along with a parameter search strategy. By including a scaled search strategy, the agent optimizes the use of different scales of observation, or fields-of-view, to increase the speed and accuracy of the landmark detection. For example, by enabling the agent to begin with a larger field-of-view, the agent may utilize greater context when searching for the landmark. The increased context of the search allows the agent to converge on the landmark location quicker. The increased context also increases the likelihood that the agent will converge on the landmark by reducing the likelihood that the agent will get "lost" in the image data while using a smaller field-of-view. Thus, the agent automatically learns object appearance and both parameter and scale search strategies simultaneously as a unified behavioral task to localize image landmarks at a higher speed and with greater accuracy.

The disclosed embodiments can be directly applied to automatic parsing of a medical image regardless of its source (e.g., equally robust for computed tomography, magnetic resonance, ultrasound, x-ray, molecular, or other modalities). As in FIG. 1, an artificial agent is generated and trained to self-develop an optimized method for efficiently identifying an anatomical landmark. Large numbers of search parameters evolve over the course of training the agent on a set of identified landmark targets. The agent begins a training set freely and randomly navigating through the image via the state space. Gradually, the agent learns a policy during training to optimize the expected reward value $r_t$ of its actions. Expected rewards are determined by the reward value of the possible actions, a, available to the agent at time, t with the goal of identifying the target landmark (via maximizing expected reward value). Actions, a, define the positional movement that occurs during state space transitions with respect to the state space's proximity to the target landmark. Sequential actions are determined and stored by the agent, and, $\nabla_w$, $\nabla_b$, and simultaneously with landmark detection, eliminating the need to hand-craft optimization criteria, image features, or exhaustive image search. The artificial agent can be applied to object detection, segmentation, tracking, and/or image registration, beneficially advancing systems based on medical imaging.

In the context of medical image parsing, disclosed embodiments provide machine driven image understanding by formulating the landmark detection problem as a generic learning task for an artificial agent. Representation learning techniques through deep learning and solutions for generic behavior learning through reinforcement learning provide a model encapsulating a cognitive-like learning of a process leading to the discovery of strategies for finding the locations of arbitrary landmarks, using only the raw image input information and the landmark annotations. Opposed to standard machine learning methods, optimization of the landmark appearance model is integrated with the location parameters in a joint behavioral optimization. The flow diagram of FIG. 2, further expands on FIG. 1. The artificial agent functions in primarily two phases, training, and testing. In the training phase, the agent learns to optimize its selection of its actions based on pre-defined landmark targets marked on input images. In the testing phase, medical images of patients are input in order for the agent to locate the pre-defined landmark targets in the manner learned by the agent during the training phase.

The disclosed embodiments advance the conventional art in machine-driven image understanding in the context of medical image parsing by formulating a landmark detection problem as a generic learning task for an artificial agent. Representation learning techniques through deep learning and solutions for generic behavior learning through reinforcement learning are provided. A goal is to encapsulate a cognitive-like learning process leading to the discovery of strategies for finding the locations of arbitrary landmarks, using only the raw input image information and the landmark annotations. Unlike conventional machine learning methods, the disclosed embodiments integrate the optimization of the landmark appearance model and the location parameters in a joint behavioral optimization framework. Reinforcement learning and deep learning may surpass human performance. A goal is to model the landmark detection problem in the context of medical image parsing as a behavioral task for an artificial agent.

Constructing artificial agents that are capable of emulating and surpassing human performance for a given task, conventionally require the use of an automatic, generic learning model observed not only in exploratory, unsupervised human cognition but also in basic reward-based animal learning methods. The artificial agent is equipped with at least two fundamental capabilities found at the core of the human and animal intelligence. At a perceptual level is the automatic capturing and disentangling of high-dimensional signal data which describes the complete situation in which the agent can find itself, while on cognitive level is the ability to reach decisions and act upon the entire observed information flow.

Accurate landmark detection is a fundamental prerequisite in medical image analysis. In one application, the disclosed method may be employed in both the contexts of cardiac magnetic resonance imaging (MRI) and cardiac ultrasound imaging, which are frequently used for structural and functional analysis of the heart. Other imaging modalities and/or anatomy may be used.

Figure 3A:
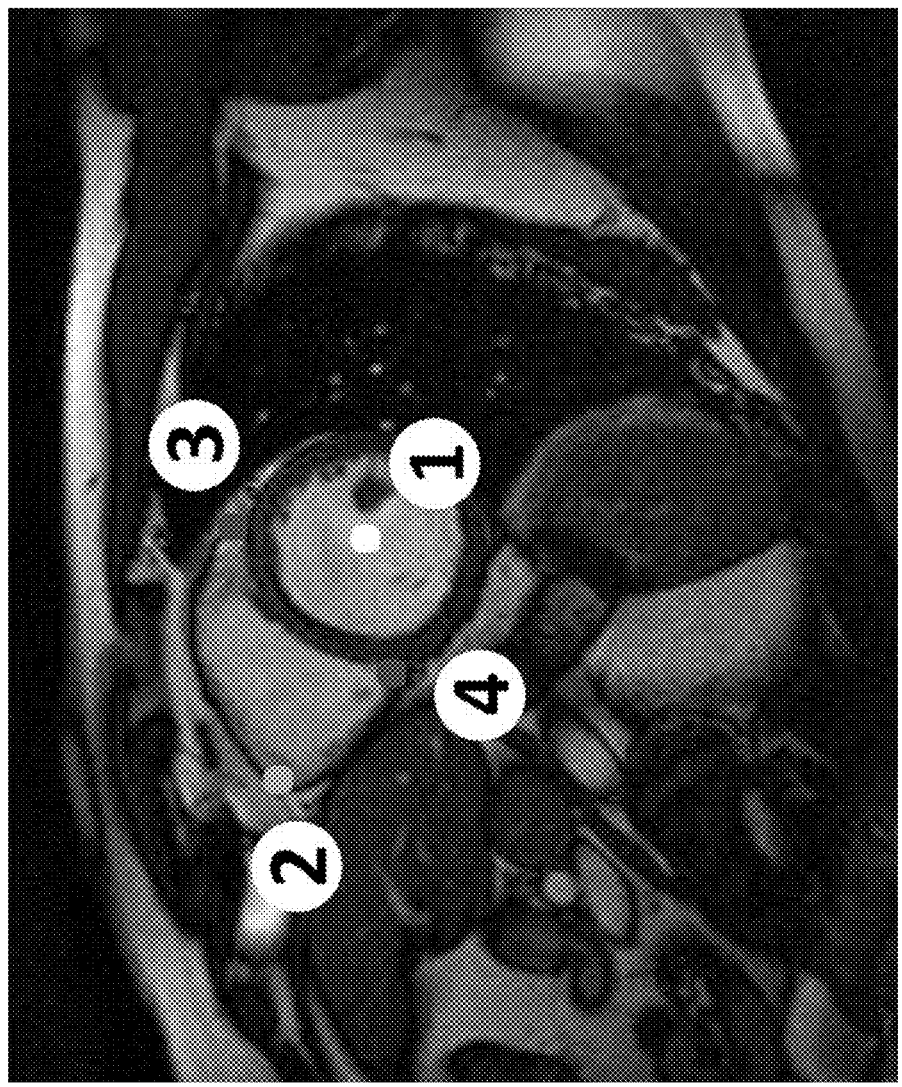
FIG. 3A depicts an exemplary short-axis cardiac MR image provide a cross-sectional view of the left and right ventricles with anatomical landmarks.

Short-axis cardiac MR images, such as FIG. 3A, provide a cross-sectional view of the left and right ventricles (LV and RV). In these types of images, particular landmarks may define important anatomical features of the heart such as the LV-center (also called left-ventricular basis central access point), the anterior RV-insertion, the posterior RV-insertion, and RV-extreme points. Accurately identifying any one or more of these or other landmarks represents a step in the context of part modeling. For example, the right ventricular insertion points and extreme point can be used to initialize the 3-D segmentation model and impose constraints on the shape of the right ventricle.

In one non-limiting example, an initial data set may contain approximately 1000 short axis view MR images acquired from several hundred different patients acquired from different vendors and formed into hundreds of training images. The training images may be preprocessed, such as resampling images to uniform, isotropic resolution (e.g. 2 mm) and normalizing the data. A cross validation set may be used to quantify the performance during training. The disclosed method achieves the goal of increased accuracy on the test set presenting more accuracy than is currently available in conventional methods.

In order to learn optimal action policy in a sequence of learning episodes, the agent is given random training images with corresponding random start-states. The agent then follows an $\in$-greedy search strategy in the selected image, generating, at the end of the episode a trajectory which is added to its experience memory. During the exploration, periodic updates are applied to the parameters of the neural network, leading to a more accurate approximation of the optimal Q* function, given the current experience. This process is repeated in an iterative manner until the detection accuracy on the validation set is minimal.

Experiments on the network architecture and training parameters are the same regardless of the dimensionality of the medical image and the medical imaging modalities that will be subjected to a trained agent. In some embodiments, the agent may be trained using root mean square (RMS)-prop mini-batch approach, which may provide the benefit of improved performance over standard stochastic gradient descent. In one example, the learning rate is set to $\eta=0.00025$, justified by the sparse sampling applied in experience replay, while the discount factor is fixed to 0.9. Other parameters important to training are the replay memory size (100000 view-patches) and $\in=0.8$ decaying linearly to 0.05.

Figure 3B:
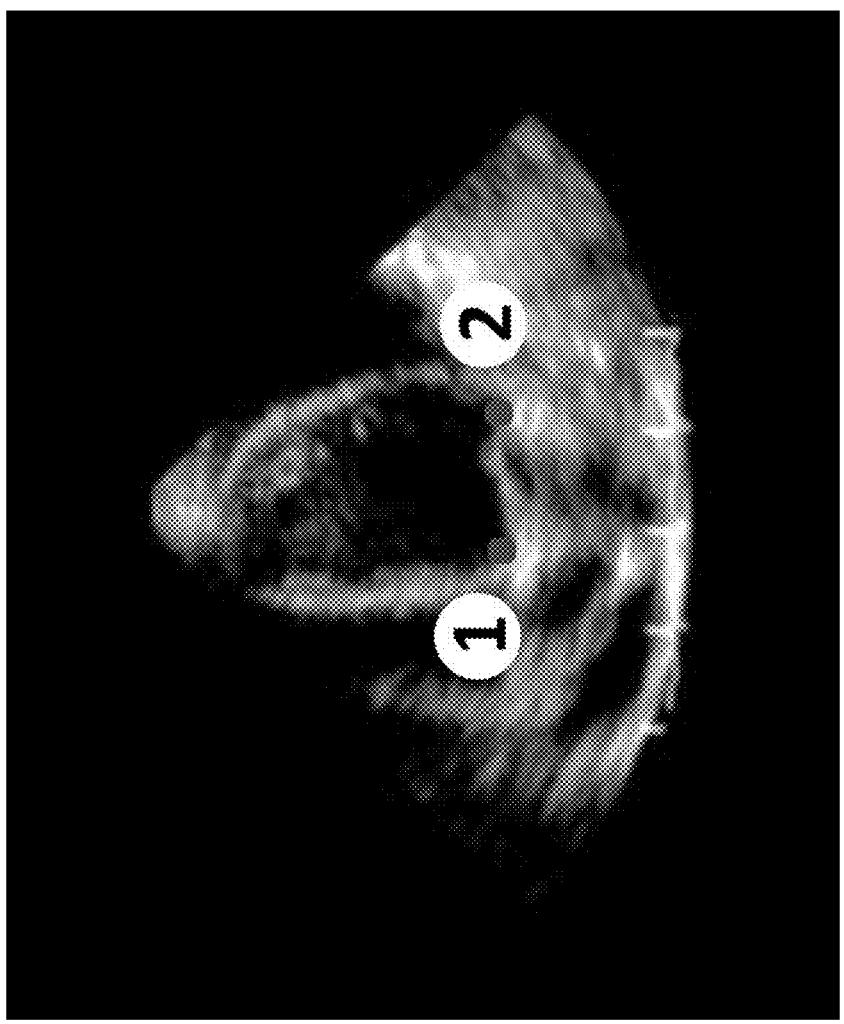
FIG. 3B depicts a cardiac ultrasound image with anatomical landmarks.
Figure 4A:
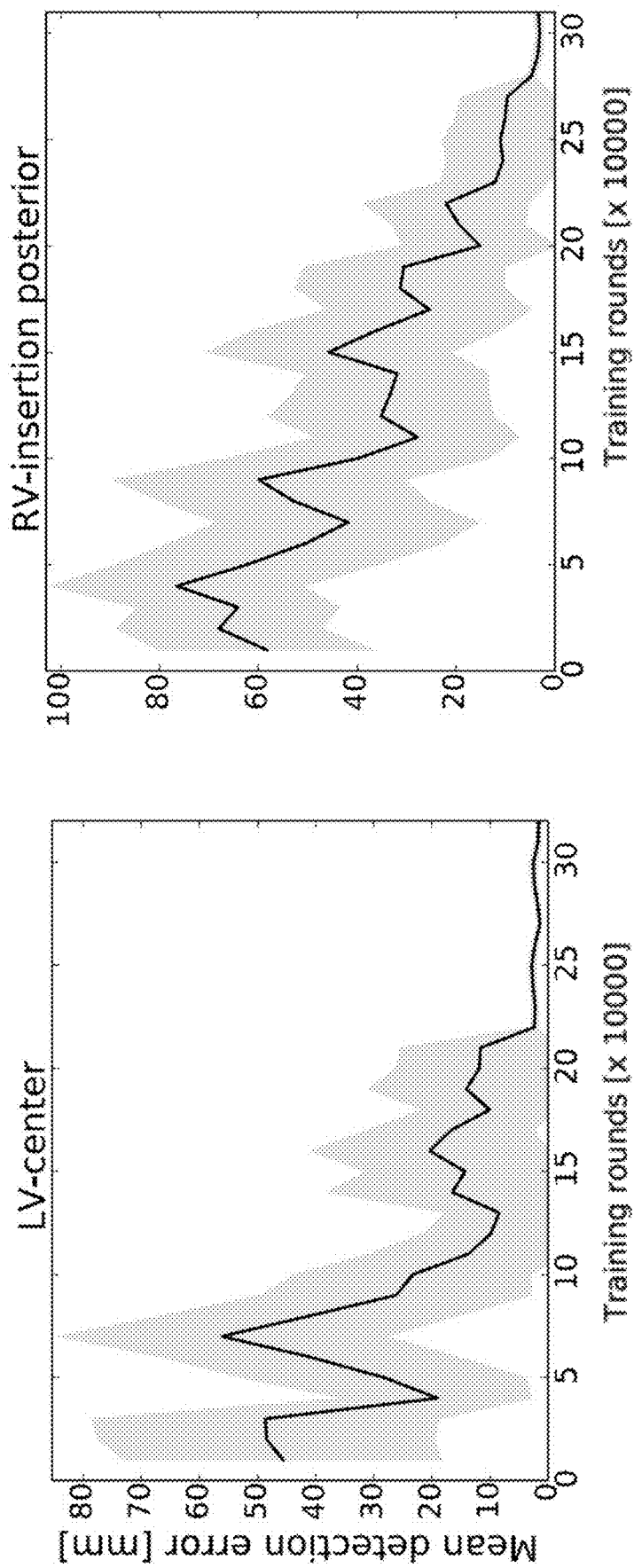
FIG. 4A illustrates average detection error for an artificial agent in accordance with embodiments for generating and/or training an artificial agent for intelligent image parsing for medical imaging.
Figure 4B:
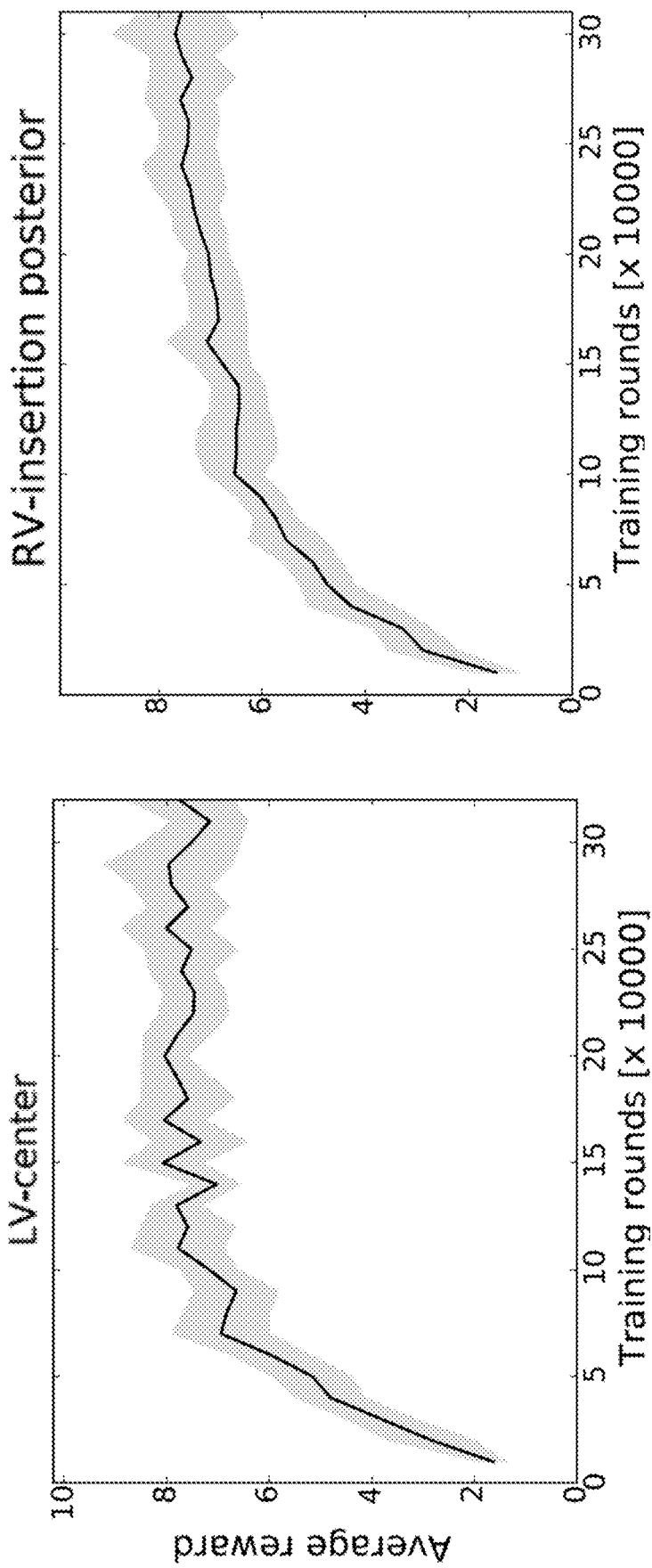
FIG. 4B illustrates average expected rewards for an artificial agent in accordance with embodiments for generating and/or training an artificial agent for intelligent image parsing for medical imaging.
Figure 4C:
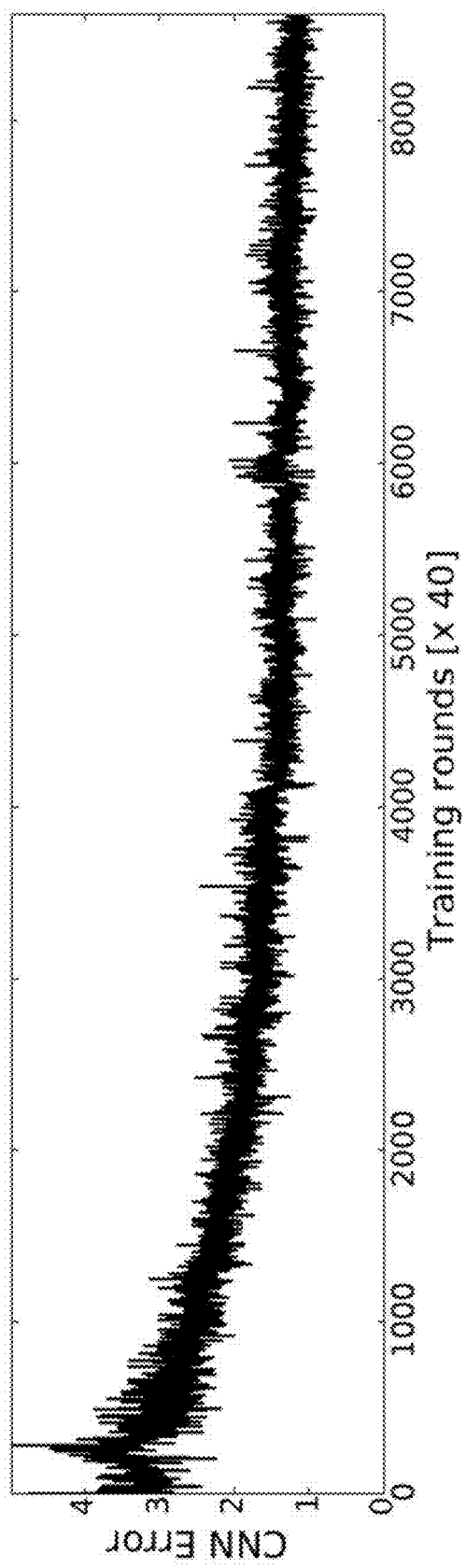
FIG. 4C illustrates CNN error for an artificial agent in accordance with embodiments for generating and/or training an artificial agent for intelligent image parsing for medical imaging.

FIG. 3A-3B illustrate various points examples significant anatomical landmarks in two different imaging modalities, MR and ultrasound, respectively. Regarding cardiac MR image FIG. 3A, landmark 1 represents the left-ventricular base central axis point (LV-center). Landmark 2 represents the right-ventricular point. Landmarks 3 and 4 represent the anterior and posterior RV-insertion points, respectively. FIG. 3B illustrates Landmark 1 of the ultrasound image as the mitral septal annulus, and landmark 2 as the mitral lateral annulus point. FIGS. 4A-4C illustrate performance evolution during artificial agent training in these two modalities. The high standard deviation of the detection accuracy is correlated with divergent trajectories, given the random initialization of the policy. However, as the policy improves, the detection accuracy increases, reaching the maximum point when all trajectories converge to the correct landmark position. Table 1 illustrates the detection error in short-axis MR images from a test set. The detection error is quantified as the distance to the ground-truth, measured in mm.

TABLE 1

| Landmark Type | Detection Error [mm] | | |
|---|---|---|---|
| | Mean | Median | STD |
| LV-center | 1.85 | 1.76 | 2.23 |
| RV-extreme | 4.94 | 4.24 | 3.65 |
| RV-insertion ant. | 3.72 | 3.05 | 2.33 |
| RV-insertion post. | 2.17 | 1.78 | 1.55 |

The plots of FIG. 4B illustrate, the average expected reward of the LV-center landmark agent and the RV-insertion posterior landmark agent, respectively, as computed for random states that are kept fixed across the training stages. The plot of FIG. 4C shows the progression of the mean squared error in the Bellman equation. The quality of the learned policy may be quantified to determine the number of training rounds based on the mean detection error on the cross-validation set. Table 2 illustrates the detection error in an exemplary analysis of cardiac ultrasound images from the test set. The detection error is quantified as the distance to the ground-truth, measure in pixels.

TABLE 2

| Landmark Type | Detection Error [pixels] | | |
|---|---|---|---|
| | Mean | Median | STD |
| Mitral septal annulus | 1.27 | 1.17 | 0.83 |
| Mitral lateral annulus | 1.62 | 1.28 | 1.40 |

During the evaluation, the agent starts in a random or predefined state (e.g. expected landmark location based on the ground truth) and follows the computed policy, iterating through the state space until an oscillation occurs (an infinite loop between two adjacent states). The end state is considered a high confidence solution for the position of the target landmark, if the expected reward $$\max_{a} Q^*(s_{target}, a) < 1 \text{ (closer than one pixel).}$$

If this is not the case, the search has failed. One benefit of the disclosed embodiments provides an effective confidence measure for the performance of the agent. FIGS. 8A-8D depict visualizations of the optimal action-value function Q*, with each state space encoding the highest expected reward, considering all actions that may be taken in that state.

In addition to detection of divergent trajectories, this confidence measure can also indicate that the landmark is not contained within the image. In one non-limiting example, trained artificial agents are applied to 100 long axis cardiac MR images from different patients. The performance evaluation determines that oscillation occurs at points where the expected future reward is significantly high as illustrated in plots of FIG. 4A. Oscillation with a significantly high expected future reward indicates the low confidence of the result. The same holds true also for divergent trajectories in images with the landmark.

Figure 5:
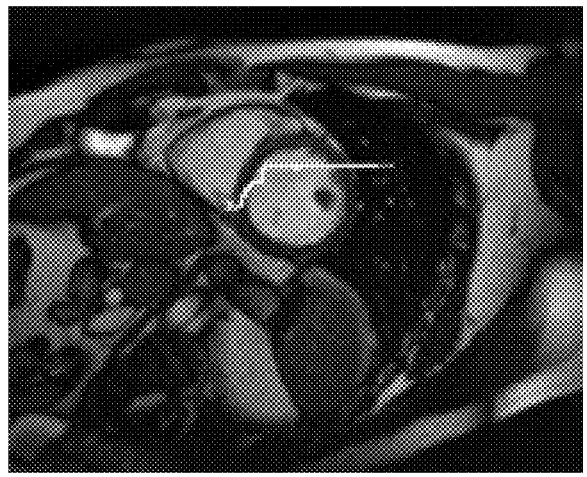
FIG. 5 illustrates example illustrations of convergence, divergence, and accuracy of convergence to a solution in accordance with disclosed embodiments.
Figure 5:
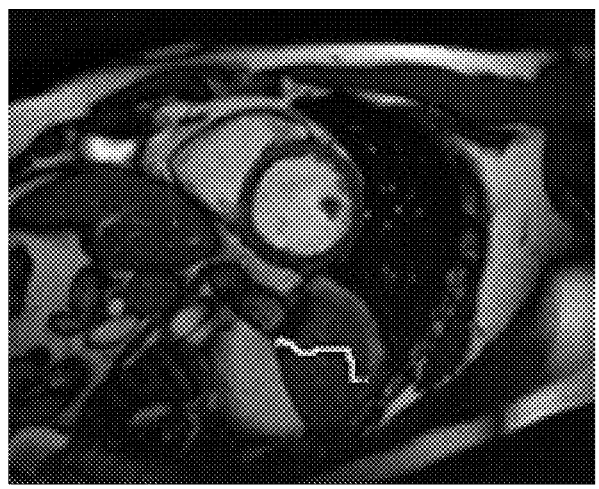
Figure 5:
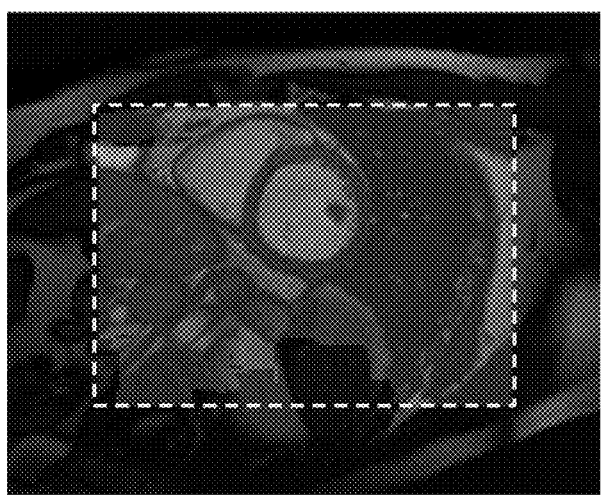

The accuracy of convergence to a solution is largely independent of the location of the beginning position of the start state in relation to the medical image. In randomly selected test images evaluated for convergence, more than 90% of the possible starting points converged to the correct solution as shown in image 520 of FIG. 5. Image 520 illustrates the boundary of the state space (limited such that image margins cannot be crossed) in dashed lines, individual starting coordinate location locations appearing as shaded regions indicating that the vast majority of possible starting points result in successful identification of the landmark target. In other words, only three random attempts can indicate a probability of diverging to a degree of less than 0.1%. FIG. 5, image 500, illustrates example trajectories converging to the landmark position. Image 510 illustrates divergence of the trajectories into a sub-optimal region. Images 500 and 510 illustrate the starting point on the right, target landmark on the left with trajectories illustrated as a white path ending at the detection result.

Figure 6:
FIG. 6 illustrates example MR trajectories in accordance with disclosed embodiments.
Figure 6:
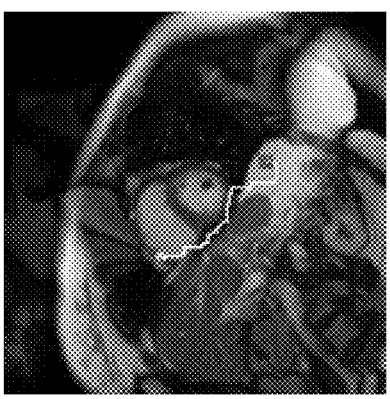
Figure 6:
Figure 6:
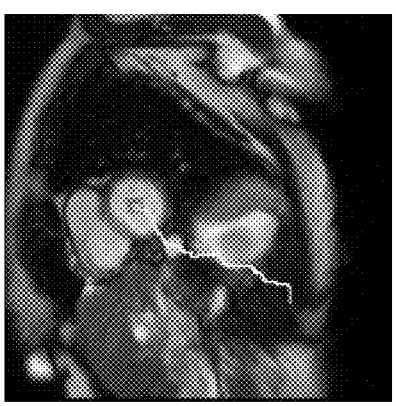
Figure 6:
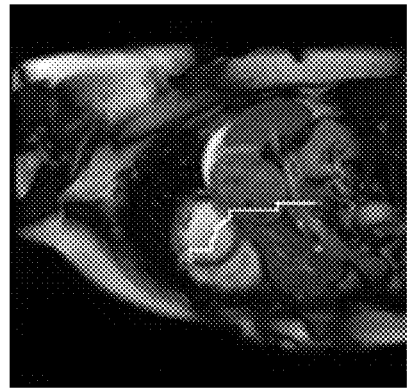
Figure 6:
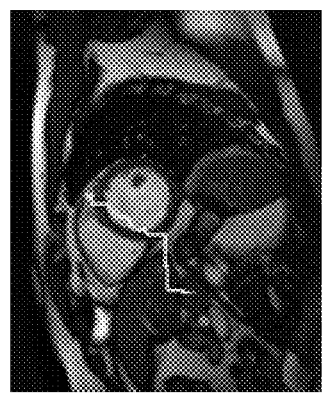
Figure 6:
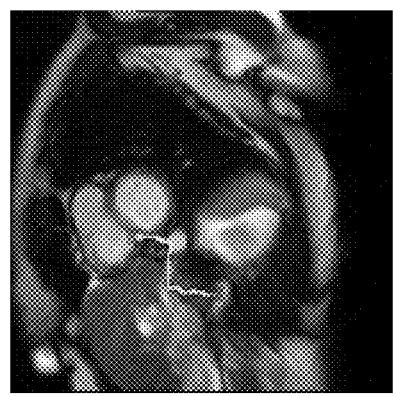
Figure 7:
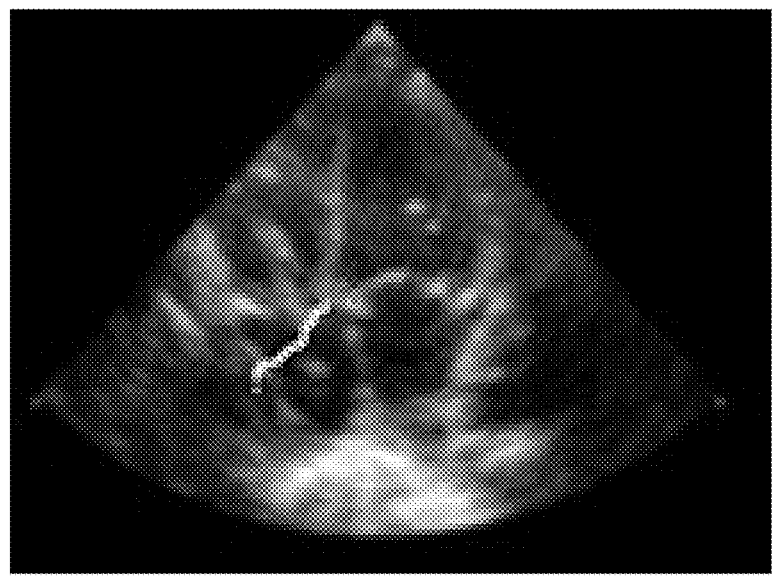
FIG. 7 illustrates example MR trajectories in accordance with disclosed embodiments.
Figure 7:
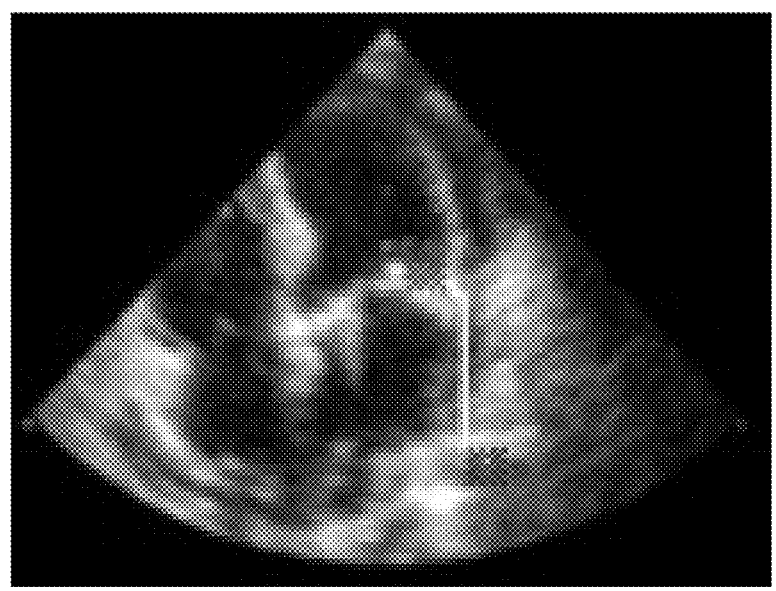
Figure 7:
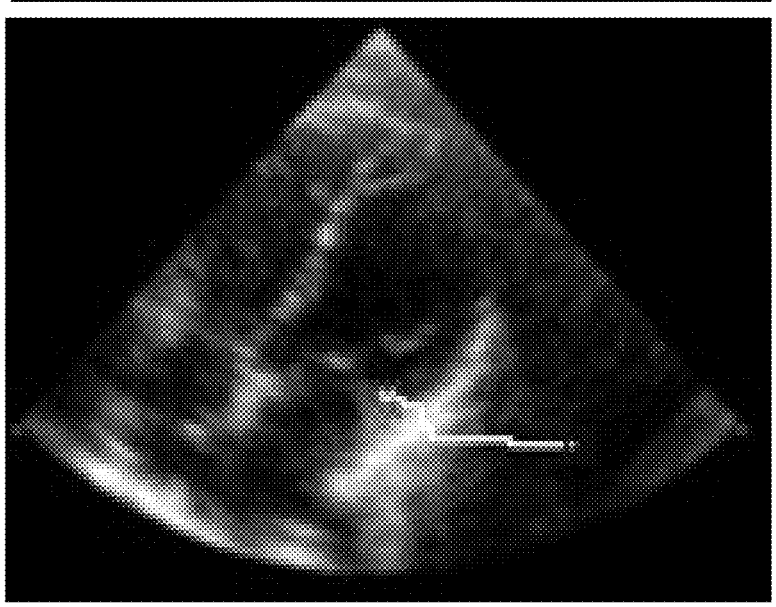

Identical learning parameters and network structure may be used with different imaging modalities. For example, the disclosed method may also be used in cardiac ultrasound imaging. Ultrasound images of a four-chamber view may have the target identification of two mitral valve annulus points: the mitral septal annulus and mitral lateral annulus points (see FIG. 3B). Here, the data set may include approximately 1000 images from several hundred patients that are used to construct randomly selected data subsets for agent training, cross-validation of the trained agent, and quantification of trained agent performance. The data sets respectively include approximately 1000 training images, 100 cross-validation, and 100 test images. Preprocessing may be applied such as normalization and resampling steps as in the cardiac MR example data set. Table 2 shows the detection error. FIG. 6 images 600-660 illustrate example trajectories as a white path in tests of an MR image for the four landmarks identified in FIG. 3A. Images 600 and 610 illustrate trajectories for the LV-center landmark with starting locations at the bottom of the images and convergence with the target landmark at the top of the images. An RV-extreme landmark is the target of image 620, with starting position of the agent at the bottom of the image and target at the top. Image 630 and 640 illustrate the posterior RV-insertion point as the target landmark. Images 650 and 660 illustrate the anterior RV insertion point. The starting position of image 630 is located at the top of the image and at the bottom of images 640, 650, and 660. FIG. 7 illustrates example trajectories of the ultrasound landmarks illustrated in FIG. 3B. The mitral septal annulus is identified as the landmark target in ultrasound image 700 and the mitral lateral annulus points are the targets of images 710 and 720. Each starting position is indicated towards the bottom of the image, with the trajectories visualized as white paths illustrating successful convergence at the top most point, the landmark target. The mean accuracy of less than 1.7 pixels with no outliers indicates the robustness of the approach on different modalities.

Deep Representation Learning

Deep learning (DL) techniques are used to generate intelligence of the artificial agent of the disclosed embodiments, allowing the artificial agent to learn (e.g., optimize behavior). DL techniques are conventionally applied to various problems ranging from image classification, object detection and segmentation, and speech rate recognition to transfer learning. Deep learning is the automatic learning of hierarchical data representations describing the underlying phenomenon. That is, deep learning proposes an automated feature design by extracting and disentangling data-describing attributes directly from the raw input in contrast to feature handcrafting. Hierarchical structures encoded by neural networks are used to model this learning approach.

Figure 2:
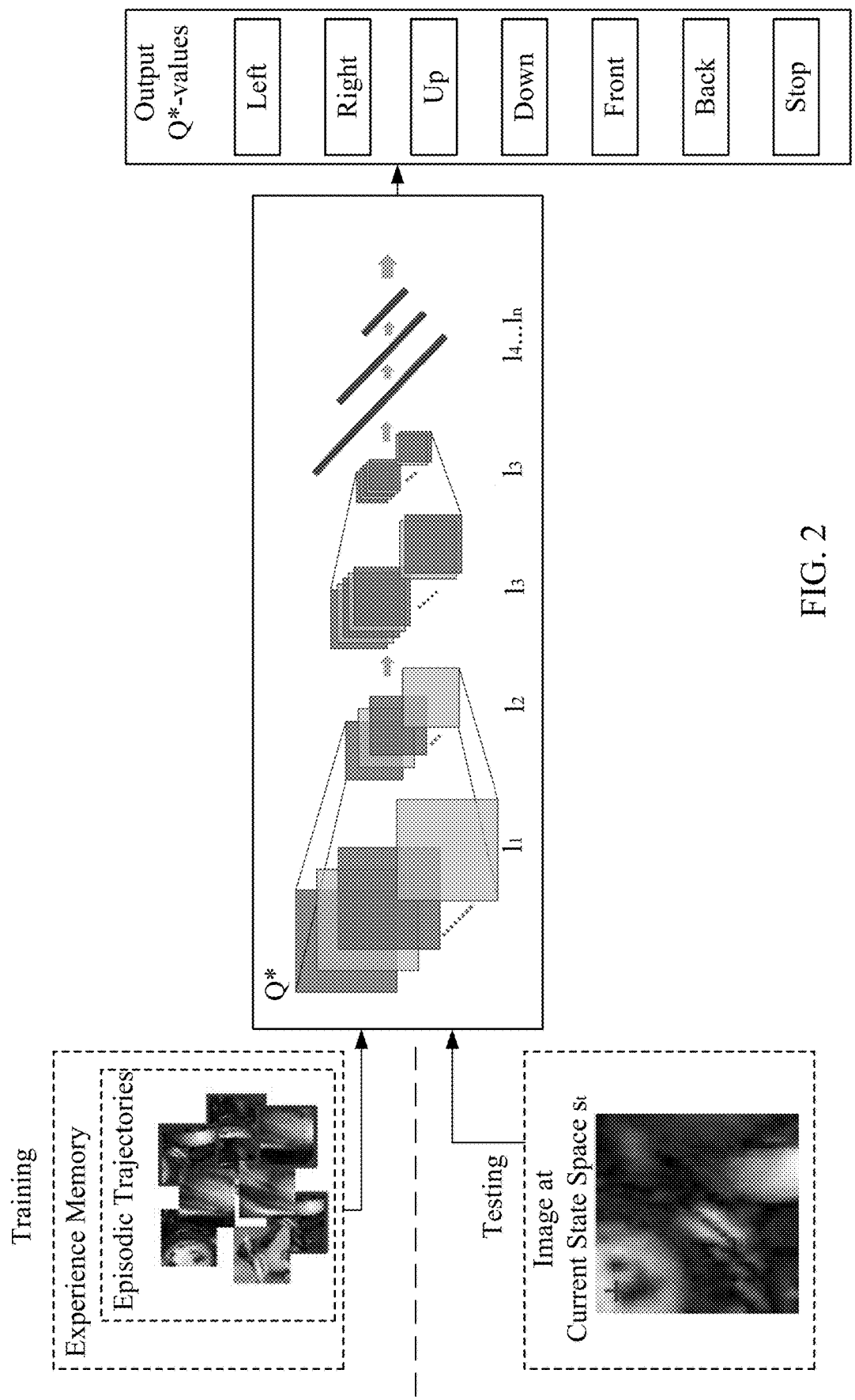
FIG. 2 illustrates another embodiment for generating and/or training an artificial agent for intelligent image parsing for medical imaging.

The convolutional neural network (CNN) mimics non-cyclic, feed-forward type of information processing observable in the early visual cortex. This learning emulates, automates, and improves the principles of animal and human receptive fields. Deep fully connected neural networks include multiple layers. Each layer learns a more abstract and insightful data representation using the output from the previous layer. Hierarchical layers of translation-invariant convolutional filter kernels are constructed based on local spatial correlations observable in images. As illustrated in FIG. 2, Convolutional Neural Network Q* includes multiple layers $l_1$-$l_n$. Convolutional layer $l_1$ may include 32 6×6 kernels feeding into 2×2 pooling-layer, $l_2$. The pooling layer then feeds into convolutional layer $l_3$ including 46, 4×4 kernels feeding into 2×2 pooling-layer $l_4$. Further layers include $l_{4-n}$, which may be fully-connected layers 512×128× 64. Q* values are output for each of the possible actions of left, right, up, and down. In another example, the Convolutional Neural Network Q* includes multiple layers $l_1$-$l_n$ for three-dimensional searching. For example, the convolutional layer $l_1$ may include 32 6×6×6 kernels feeding into 2×2×2 pooling-layer, $l_2$. The pooling layer then feeds into convolutional layer $l_3$ including 46, 4×4×4 kernels feeding into 2×2×2 pooling-layer $l_4$. Further layers include $l_{4-n}$, which may be fully-connected layers 512×128×64. Q* values are output for each of the possible actions of left, right, up, down, front, back and stop. Additional actions may be included, such as increasing or decreasing the resolution of a view patch of the image.

The application of the filter kernel to the data generates a representation of the filtered data at each layer, called a representation map. The representation map generated by the l-th convolutional filter kernel in the layer k by $\vec{\omega}^{(k,l)}$, is represented by Equation 1:

$$o_{i,j} = \sigma\left(\left(\vec{\omega}^{(k,l)} * \vec{x}\right)_{i,j} + b^{(k,l)}\right) \qquad \text{Eq. 1}$$

where x is the representation map from the previous layer used as input for the l-th convolutional filter kernel, (i,j) defines the evaluation location of the filter and $b^{(k,l)}$ is the bias of the considered output neuron. The function σ represents the activation function used to synthesize the input information. Possible alternatives to the above activation function may be selected based on the given learning problems. Examples of learning problems include classification, multi-class classification or regression, and example alternative functions include the sigmoid function, hyperbolic tangent, or rectified linear units (ReLU).

Given a set of scalar or matrix data of independent observations "•", such as input patches $\vec{X}$, and corresponding value assignments $\vec{y}$, the network response function may be defined as $R(•; \vec{\omega}, \vec{b})$. Thus, a Maximum Likelihood Estimation to estimate the optimal parameters for the CNN results as Equation 2:

$$\vec{\omega}, \vec{b} = \underset{\vec{\omega},\vec{b}}{\text{argmax}} L(\vec{\omega}, \vec{b}) = \underset{\vec{\omega},\vec{b}}{\text{argmin}} \|R(\vec{X}; \vec{\omega}, \vec{b}) - \vec{y}\|_2^2 \quad \text{Eq. 2}$$

The optimization may be solved with the Stochastic Gradient Descent (SGD) method or rms-prop in a mini-batch approach. Using a random set of samples $\vec{X}$ from the training input, a feed-forward propagation is performed to compute the network response $R(\vec{X}; \vec{\omega}, \vec{b})$. Denoting $\vec{b}(t)$ and $\vec{b}(t)$, the network parameters in the t-th optimization step are updated according to Equation 3:

$$\vec{\omega}(t+1) = \vec{\omega}(t) - \eta \nabla_w E(\vec{X}; \vec{\omega}(t), \vec{b}(t))$$

$$\vec{b}(t+1) = \vec{b}(t) - \eta \nabla_b E(\vec{X}; \vec{\omega}(t), \vec{b}(t)), \quad \text{Eq. 3}$$

where $\nabla$ is the gradient of the cost function with respect to the network parameters, $\eta$ the magnitude of the update. That is, the learning rate, and $E(\vec{X}; \vec{\omega}(t), \vec{b}(t)) = \|R(\vec{X}; \vec{w}, \vec{b}) - \vec{y}\|_2^2$ represents the error function. Backpropagation may be used to compute and apply the gradient to the network parameters.

Reinforcement Learning

The disclosed embodiments use DL in conjunction with Reinforcement learning (RL). RL is a technique facilitating learning as an end-to-end cognitive process for an artificial agent, instead of a predefined methodology. One RL setting is composed by an artificial agent that can interact with an uncertain environment (e.g., medical image of a patient without landmark target identified) with the target of reaching pre-determined goals (e.g., identifying the landmark target in the image). The agent can observe the state of the environment and choose to act on the state, similar to a trial-and-error search, maximizing the future reward signal received as a response from the environment. The main system diagram of FIG. 1 illustrates an artificial agent interacting with portions of an image defined by a mobile state space $s_t$. Optimal action-value function approximator Q* estimates the agent's response to image data as measured by state space $s_t$, in the context of a reward function $r_t$. This reward-based decision process is modeled in RL theory as a Markov Decision Process (MDP) defined by a tuple M:=S, A, T, R, γ, where S is a finite set of states and $s_t \in S$ is the state of the agent at time t. A is a finite set of actions allowing the agent to interact with the environment, and $a_t \in A$ is the action the agent performs at time t. $T:S \times A \times S \rightarrow [0; 1]$ is a stochastic transition function, where $T_{s,a}^{s'}$ is the probability of arriving in state s' after the agent performed action a in state s. $R: S \times A \times S \rightarrow \mathbb{R}$ is a scalar reward function, where $R_{s,a}^{s'}$ is the expected reward after a state transition. γ is the discount factor controlling the importance of future versus immediate rewards.

The future discounted reward of an agent at time $\hat{t}$ can be written as $$R_{\hat{t}} = \sum_{t=\hat{t}}^{T} \gamma^{t-\hat{t}} r_t,$$

with T marking the end of a learning episode and $r_t$ defining the immediate reward the agent receives at time t. In model-free reinforcement learning, the target may be to find the optimal so-called action-value function, denoting the maximum expected future discounted reward when starting in state s and performing action a as in Equation 4:

$$Q^*(s, a) = \max_{\pi} \mathbb{E}[R_t | s_t = s, a_t = a, \pi] \quad \text{Eq. 4}$$

where π is an action policy. That is, the action policy is a probability distribution over possible actions in each given state. Once the optimal action-value function is estimated, an optimal action policy determining the behavior of the agent can be directly computed in each state as Equation 5:

$$\forall_s \in S : \pi^*(s) = \underset{a \in A}{\text{argmax}} Q^*(s, a) \quad \text{Eq. 5}$$

The optimal action-value function approximator Q* is the Bellman optimality equation, representing a recursive formulation of Equation 4, defined as Equation 6:

$$Q^*(s, a) = \sum_{s'} T_{s,a}^{s'} \left( R_{s,a}^{s'} + \gamma \max_{a'} Q^*(s', a') \right) \quad \text{Eq. 6}$$

where s' defines a possible state visited after s, a' the corresponding action and r represents a compact notation for the current, immediate reward. Viewed as an operator τ, the Bellman equation defines a contraction mapping. Applying $Q_{i+1} = \tau(Q_i), \forall(s, a)$, the function $Q_i$ converges to Q* at infinity. This standard, model-based policy iteration approach is, however, not feasible in practice. An alternative is the use of model-free temporal difference methods, typically Q-Learning, which exploits correlation of consecutive states, is more applicable in practice. Using parametric functions to approximate the Q-function furthers a goal of higher computational efficiency. Considering the expected non-linear structure of the action-value function, neural networks represent a sufficiently powerful approximation solution.

System Operation

The landmark detection problem is addressed by developing an artificial agent characterized as a reinforcement learning problem. The artificial agent learns (e.g., develops the landmark detection solution) during training with a set of N training images $I_1, I_2, \ldots, I_N$. Each contains M annotated landmarks. Focusing on one particular landmark indexed in each training example, the method trains an artificial, intelligent agent that can automatically discover strategies for finding the chosen landmark not only in the provided data, but also in unseen examples. The problem is defined as a Markov Decision Process M:=(S, A, T, R, γ). The state and action spaces are specified and the reward system is defined. Transition probabilities T are unknown in the disclosed, model-free embodiment.

Figure 9:
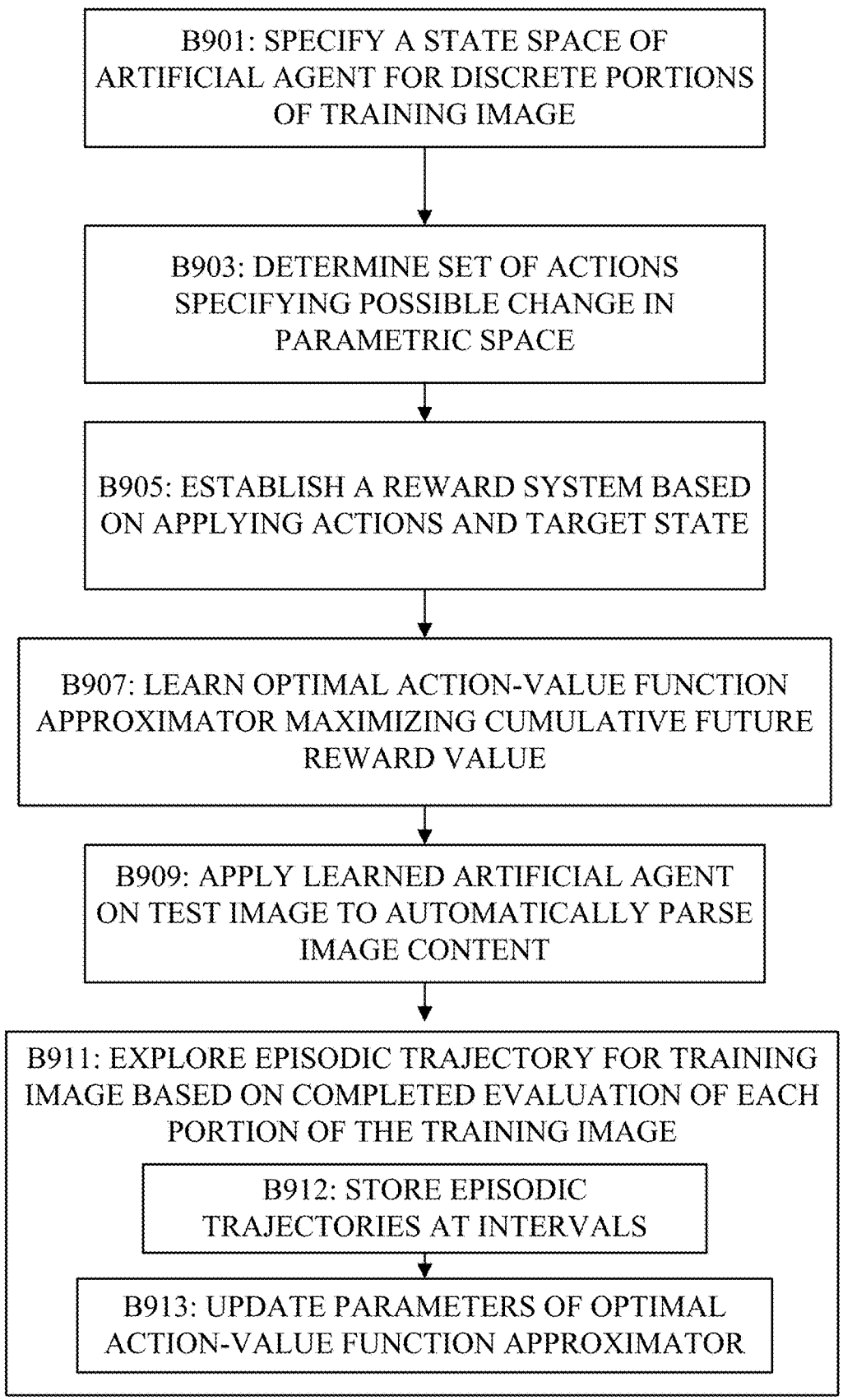
FIG. 9 illustrates a flow diagram in accordance with one disclosed embodiment for generating an artificial agent for intelligent image parsing.

The depicted methods of FIGS. 9-12 and 14-16 may be executed by imaging system 48 and/or processor 50. Program data, input, intermediate or output data may be partially or completely stored on Memory 52, FIG. 9 illustrates a flow diagram in accordance with one disclosed embodiment for generating an artificial agent for intelligent image parsing. The acts are performed in the order shown or other orders. Additional, different, or fewer acts may be provided. For example, the method is performed without act B911.

The method disclosed in FIG. 9 depicts a flow chart for intelligent image parsing. In act B901, a state space of an artificial agent is specified for discrete portions of a training image. For example, the state space has a length and width expressed as a number of pixels, with a focal point defined as the center coordinate of the set of pixels. In act B903, a set of actions is determined, each action specifying a possible change in a parametric space with respect to the test image. The set of action may include changing a position, an orientation, a scale, or a shape of the current state. The set of actions may be defined as any possible incremental changes in position of the state space that can be made by the agent. For example, a set of actions may be defined as movements of the state space position one pixel in each direction that the agent may select from the set of upwards, downwards, left, or right. The set of actions may additionally include an action in which state space remains in the same position without movement. The set of actions may be selected to provide optimal sets of measurements during agent training.

In act B905, a reward system is established based on applying each action of the set of actions and based on at least one target state. A reward value is determined by the value of the agent's selection of an action. Success is determined by the proximity of the current state space to the target state (e.g., landmark target). The target state may be an anatomical landmark with the state space defined by the position parameters of the anatomical landmark. The associated reward value may be indicative of a proximity of a current state space to the at least one target state. For example, the reward value may be ±1 for each action. The reward value of a single move can be any fractional proportion expressing the reward of the action. That is, an agent selecting an upward action has a maximum reward value when the focal point of the state space is vertically below the landmark target. When the focal point of the state space is neither exactly above, below, left, or right of the focal point of the state space, a maximum reward value cannot be attained by any upward or downward action because the set of actions is limited to upward, downward, left, and right movements at increments of one pixel.

In act B907, an optimal action-value function approximator is learned by the artificial agent. The optimal action-value specifies the behavior of the artificial agent in order to maximize a cumulative future reward value based on the reward system. The behavior of the artificial agent is a sequence of actions moving the agent towards the at least one target state. The behavior of the artificial agent is self-determined such that the agent selects a next action to change the position in the state space on the landmark target of the medical image to maximize the total cumulative future reward. The maximized reward may, but not necessarily, minimize the total number of actions that must be taken by the agent to reach its goal of identifying the location of a target landmark within an image.

In act B909, the learned artificial agent is applied on a test image to automatically parse image content. The learned artificial agent can thus identify the target state and/or if the target state does not exist within the test image. The test image, unlike the training image, does not have any predetermined target states identified and may not contain a target state (e.g., landmark target) at all. Test images may be, but are not limited to, medical image scans of patients.

An episodic trajectory is explored in act B911 for a training image based on the completed evaluation of each portion of the training image via the state space. The episodic trajectory is indicative of the actions of the artificial agent as a sequence of visited states of the training image. Act B911 may be conducted by storing, in act B912, episodic trajectories at pre-defined intervals of sequential completed evaluations of training images by the artificial agent and updating, in act B913, parameters of the optimal action-value function approximator based on the stored episodic trajectories.

Figure 10:
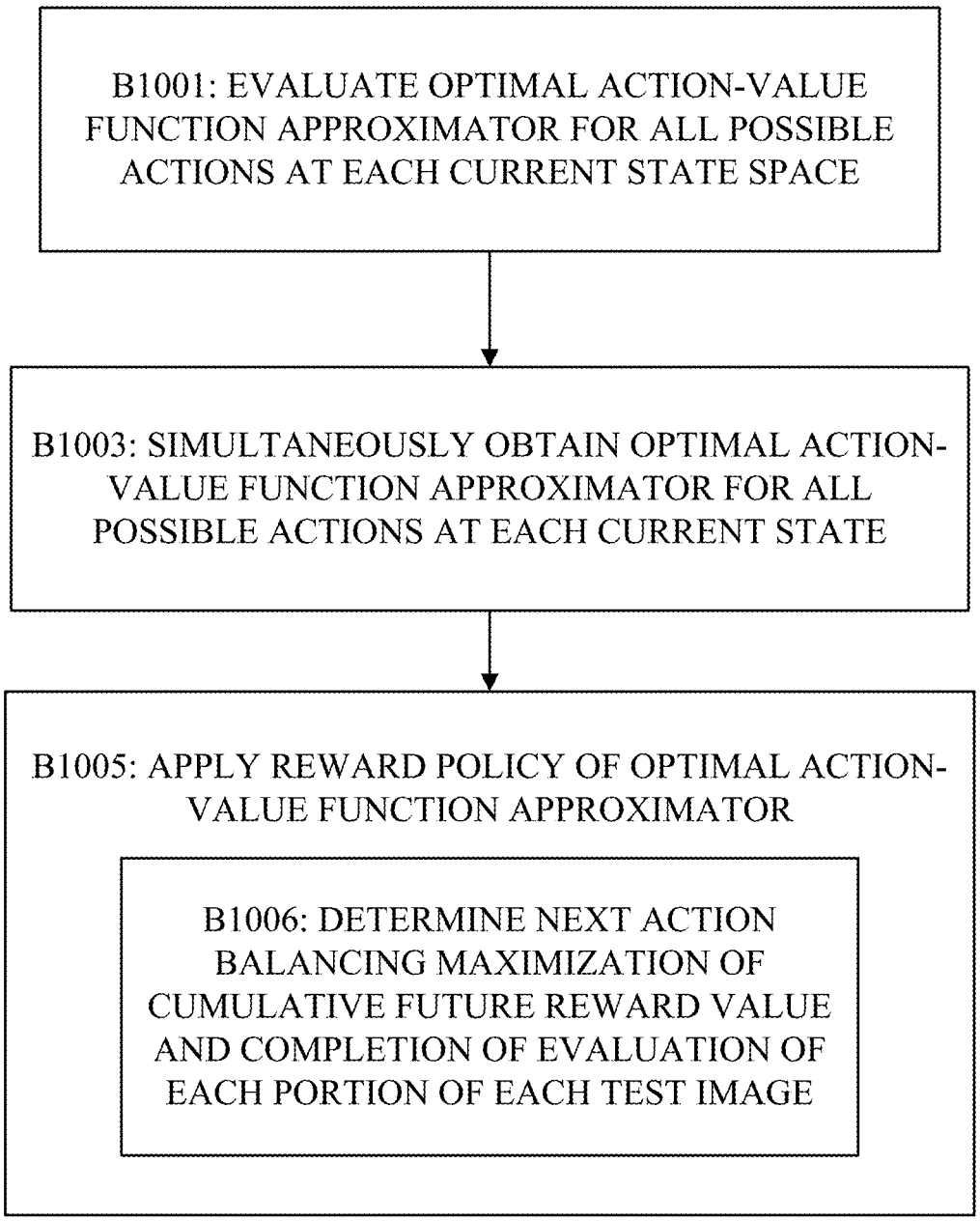
FIG. 10 illustrates a flow diagram in accordance with additional embodiments for generating an artificial agent for intelligent image parsing.

FIG. 2 illustrates a flow diagram in accordance with disclosed embodiments for generating an artificial agent for intelligent image parsing. The acts are performed in the order shown or other orders. Additional, different, or fewer acts may be provided. For example, the act B1005 may be performed in a different way than provided by act B1006. FIG. 10 illustrates acts that may be performed as part of defining the optimal action-value function approximator (act B907) of the method of FIG. 9 including a reference update delay feature of the defined optimal action-value function approximator of act B907 in FIG. 9. Accordingly, FIG. 10 may be performed as part of the method of FIG. 9.

In act B1001, the optimal action-value function approximator is evaluated for each current position of the state space. In act B1003, the optimal action-value function approximator is simultaneously obtained for all possible actions in each current state space. In act B1005, a reward policy of the optimal action-value function approximator is applied. Applying the reward policy of the optimal action-value function approximator of act B1005 may optionally include act B1006, in which the next action of the artificial agent is determined based on a balance of maximization the cumulative future reward value based on the reward system and completion of evaluation of each portion of each training image based on the state space.

Figure 11:
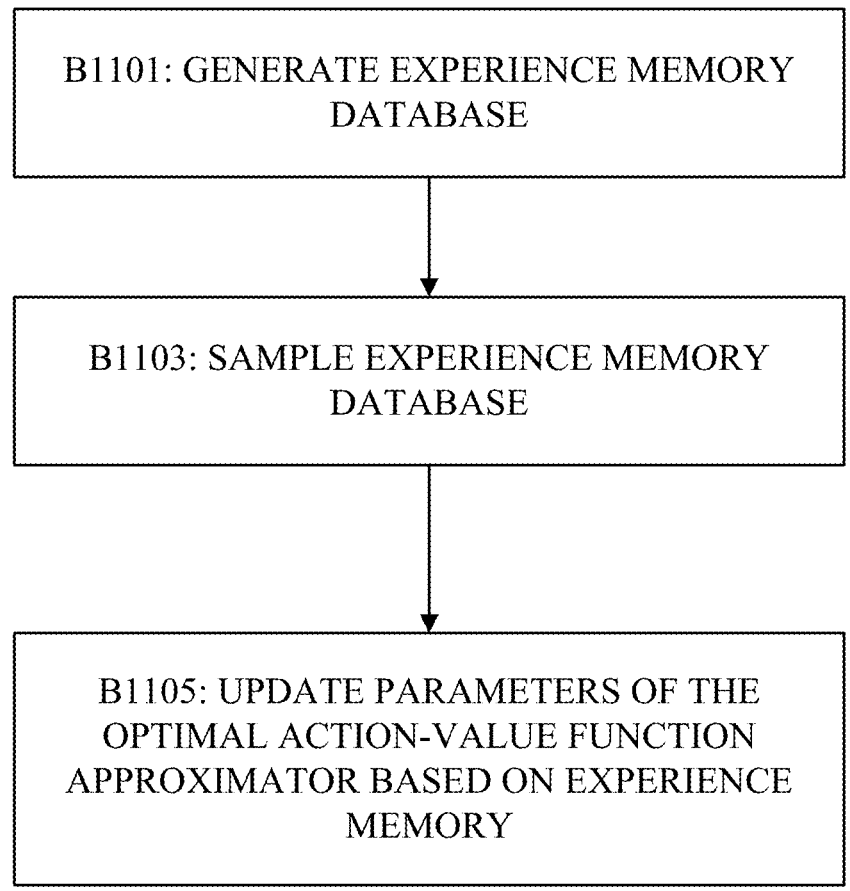
FIG. 11 illustrates a flow diagram in accordance with another embodiment for generating an artificial agent for intelligent image parsing.

FIG. 11 illustrates a flow diagram in accordance with another embodiment for generating an artificial agent for intelligent image parsing. The acts are performed in the order shown or other orders. Additional, different, or fewer acts may be provided. For example, the acts of FIG. 11 may be performed as part of the method of FIG. 9 and/or FIG. 10. FIG. 11 illustrates acts that may be performed in conjunction with the method including an experience replay feature that may be included in defining the optimal action-value function approximator. In act B1101, experience memory database is generated including a pre-defined number of last evaluated states for current training image. In act B1103, the experience memory database is sampled. In act B1105, parameters of the optimal action-value function approximator are updated based on the experience memory. Experience memory may be partially or completely stored on memory 52.

Figure 12:
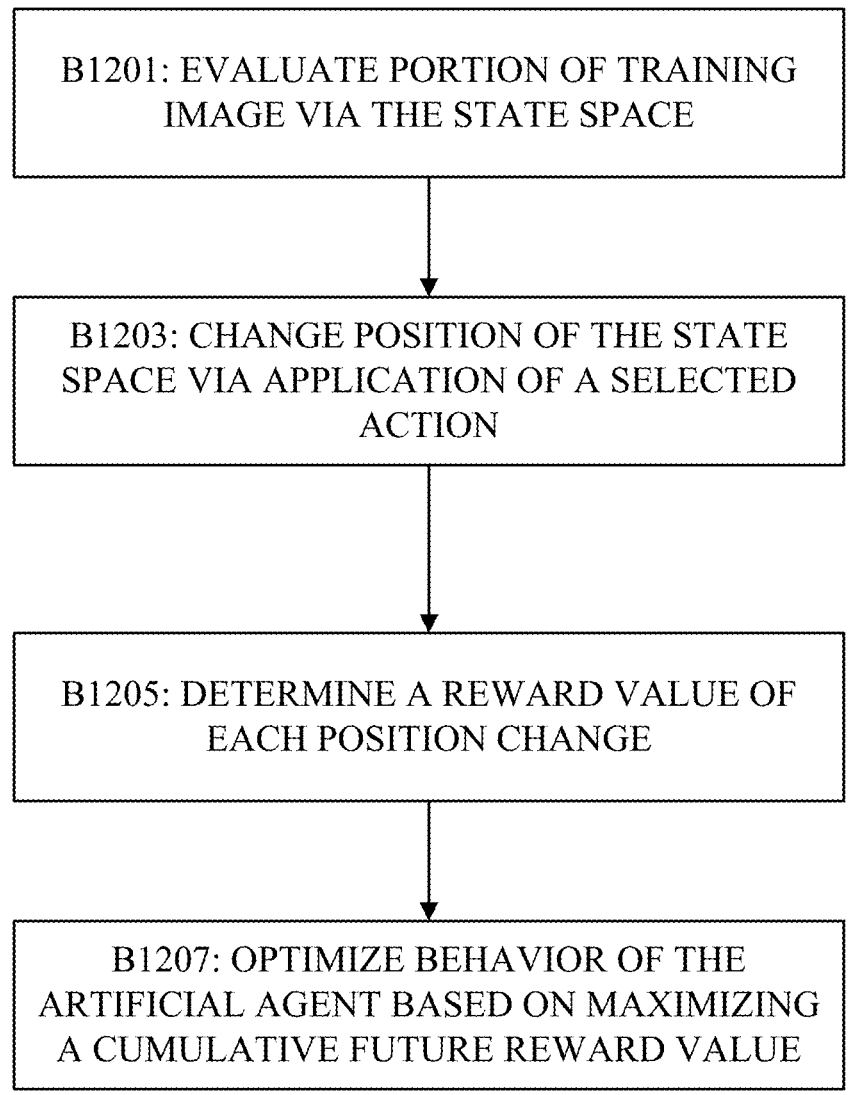
FIG. 12 illustrates a flow diagram in accordance with an embodiment of a method for training the artificial agent for intelligent landmark identification in medical images.

The methods of FIGS. 9-11 provide method for intelligent landmark identification in medical images. The artificial agent is trained using a set of test images to optimize the behavior of the artificial agent and train the artificial agent to recognize a specific anatomical landmark target using marked examples of the anatomic landmark target on each training image. FIG. 12 illustrates a flow diagram in accordance with an embodiment of a method for training the artificial agent of the preceding figures for landmark identification in medical images. The acts are performed in the order shown or other orders. Additional, different, or fewer acts may be provided. For example, the training method of FIG. 12 may be conducted as part of the method of one or more of FIGS. 9-11.

Regarding FIG. 12, in act B1201, the state space of discrete portions of each training image of a set of training images are evaluated within the position of the state space. Training images include a landmark target pre-marked on each training image. Landmark targets are pre-marked in the training data set prior to training of the artificial agent. Once trained, the artificial agent may be used to evaluate medical images of patients in order to identify the same landmark target for which the artificial agent was trained. In act B1203, a position of the state space is changed with respect to the training image via application an action of a pre-defined set of actions. In act B1205, a reward value of each position change of the state space is determined. The reward value is based on a proximity of the current state space to a pre-defined landmark target of the training image. In act B1207, behavior of the artificial agent is optimized based on maximizing a cumulative future reward value based on the reward system, the set of actions, the state space, and a set of training images. The behavior of the artificial agent is the intelligent selection of next actions that achieve a position of the state space on a landmark target in a medical image of a patient in such a way that the cumulative future reward is maximized. That is, the artificial agent learns to determine the most favorable sequence of position changes required to accurately detect a landmark target.

In one embodiment, medical images are evaluated by an artificial agent. Medical images of a patient are received by processor 50. Images may be captured via imaging system 48, stored in memory 52 or obtained over a wireless or wired network. The processor 50 applies optimized behavior of an artificial agent. The applied behavior includes selecting actions from a pre-defined set of actions changing the position of the state space relative to the medical image. Applied behavior may include evaluating discrete portions of the medical image defined by a position of the state space of the artificial agent relative to the medical image, and determining a location of the target landmark when present in the medical image from the evaluation. The identified landmark, medical image and/or other information obtained during analysis by processor 50 may be displayed on display 54. User interaction with the resulting located target landmark or image may be annotated via user input to display 54 or via a peripheral device connected to processor 50. Determination of a location of the target landmark may include identifying oscillations of the artificial agent between adjacent state space positions. The cumulative reward value of the artificial agent of the adjacent state space positions of the identified oscillations may further be determined. The landmark target may then be identified on the medical image of the patient when the cumulative reward value indicates a proximity of the adjacent state space within a pre-defined reward threshold distance value of the landmark target on the medical image. An indication that the boundary of a target space (e.g., target anatomical object) is partially or fully within the medical image.

The target landmark is not present in the medical image when the cumulative reward value is outside a pre-defined failure threshold distance value. An indication may be generated indicating that the target landmark is not present in the medical image.

Figure 19:
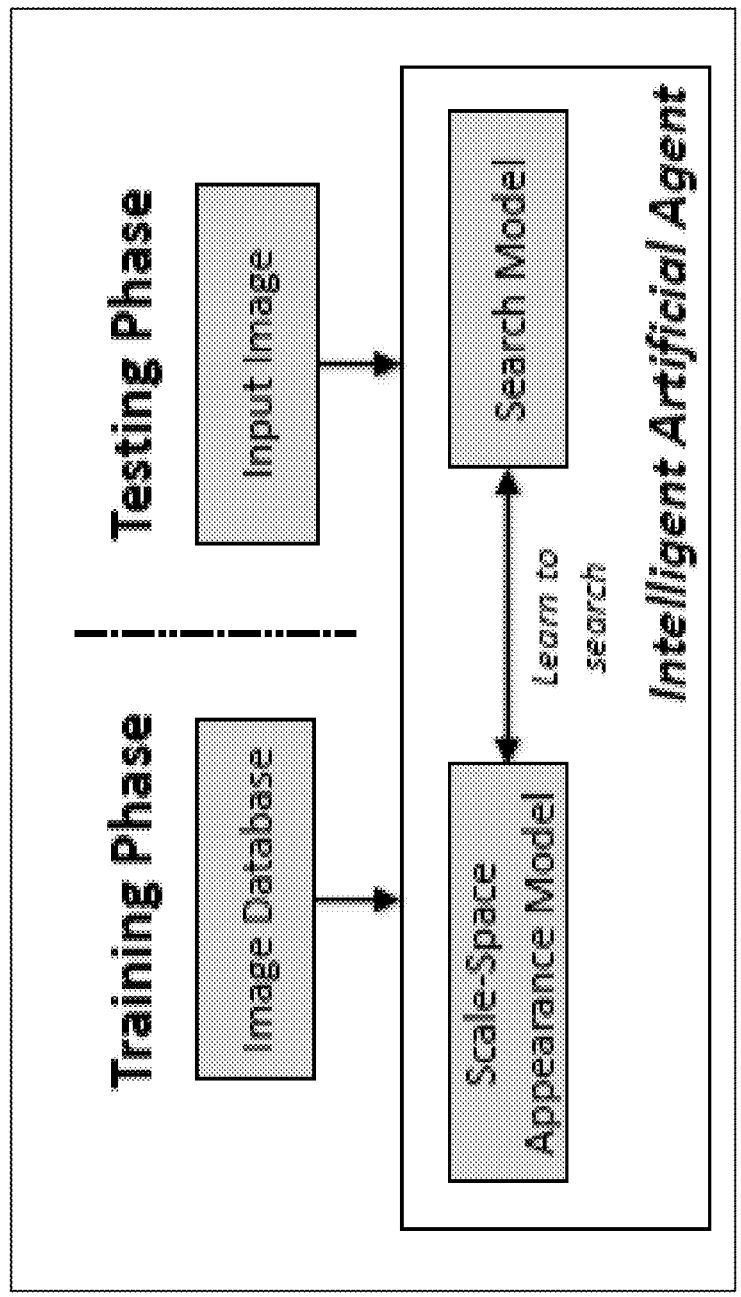
FIG. 19 illustrates an overview of machine-learning for multi-scale anatomical landmark detection.

The landmark detection problem is further improved by developing an artificial agent for searching two-dimensional images and three-dimensional volumes at multiple scales. Using the mechanism of deep reinforcement learning combined with concepts from scale-space theory multi-scale search strategies (e.g., search trajectories) in image scale-space that converge to the location of the sought anatomical landmark. Referring to FIG. 19, a schematic overview is provided for a machine-learning based paradigm for multi-scale anatomical landmark detection. The landmark detection process learns a search-strategy in a scale-space representation of a given image or from multiple images in an image database. The artificial agent learns both the image appearance and the optimal multi-scale search strategy for finding a specific anatomical structure. As discussed above, state and action spaces are specified and a reward system is defined. For example, additional actions are provided to allow navigation from coarse to fine scale levels, such as by defining two scale-space actions (e.g., zoom-in and zoom-out) in addition to defined parametric-space actions (e.g., upward, downward, left, right, forward, and backward). After navigating the parametric-space at a particular scale, the artificial agent may increase the resolution of the search by performing a scale-space action in order to navigate the parametric-space at the higher resolution.

Figure 13:
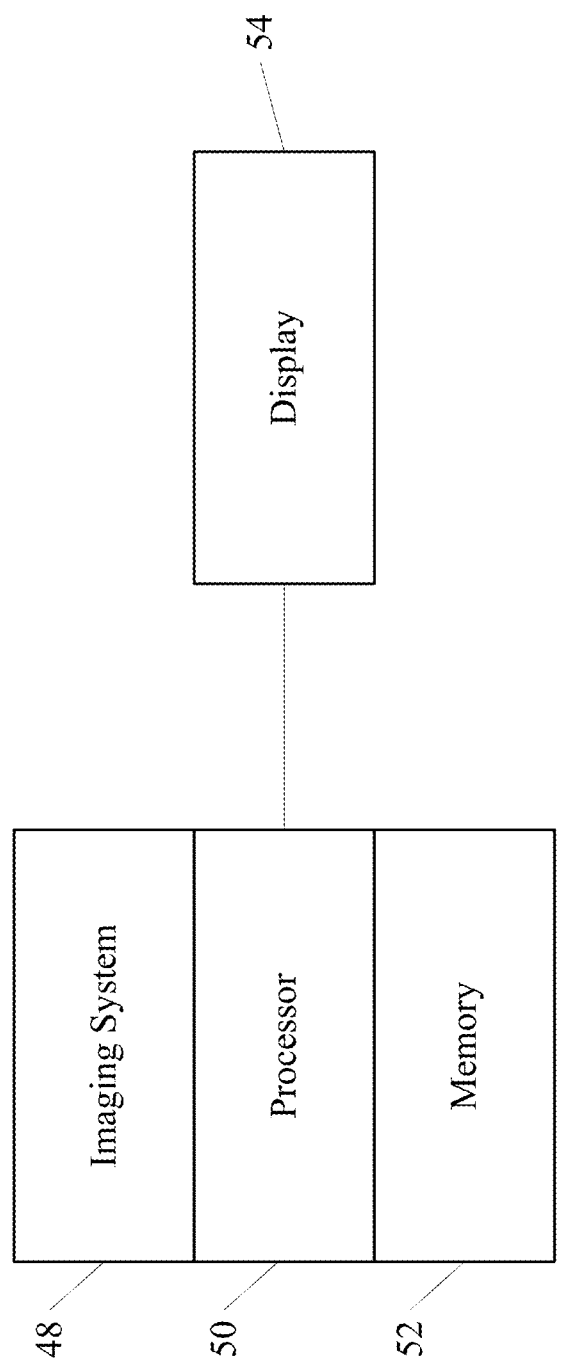
FIG. 13 illustrates an example system for intelligent landmark identification in medical images.
Figure 14:
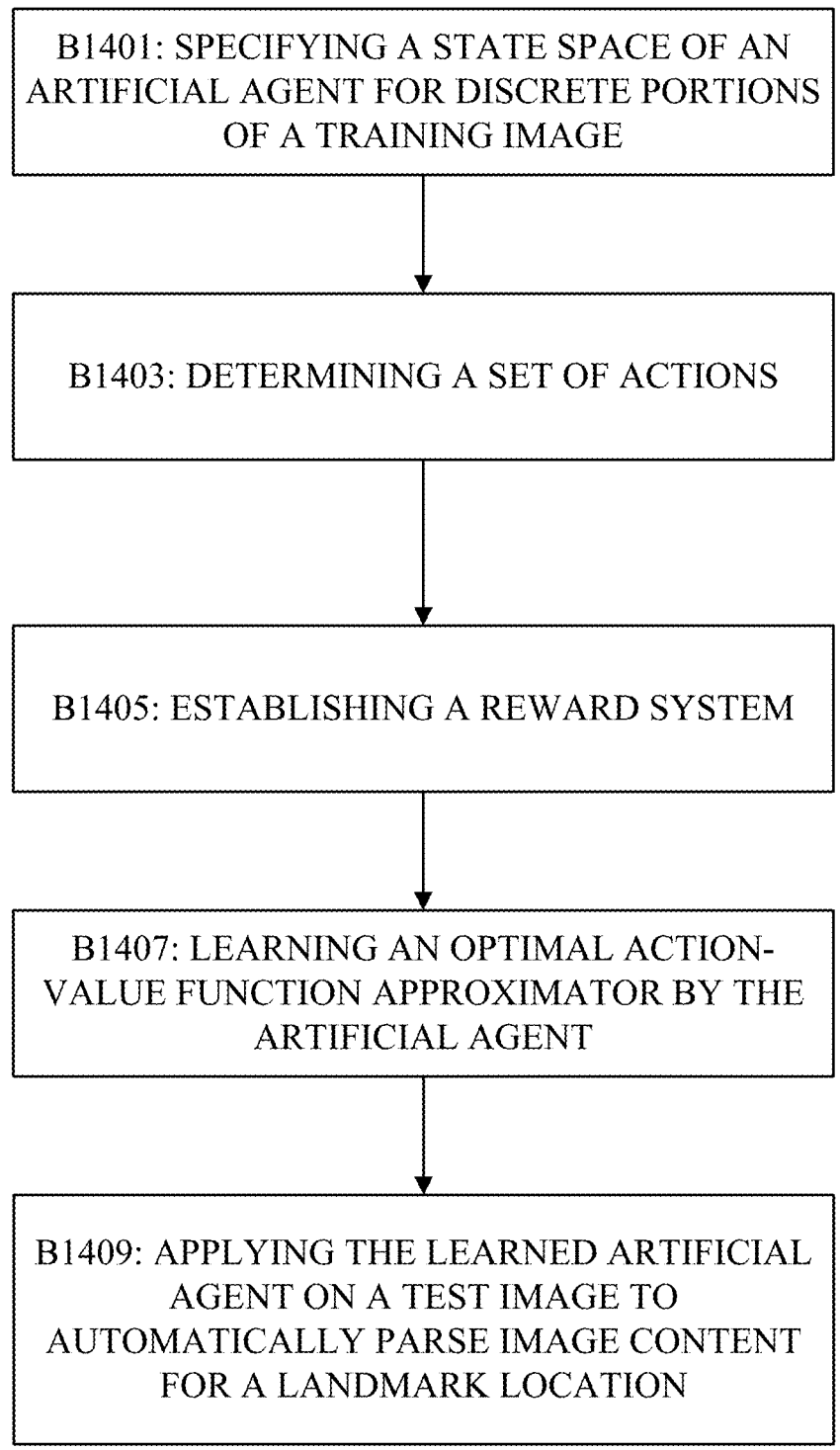
FIG. 14 illustrates a flow diagram in accordance with an embodiment for intelligent multi-scale image parsing.

FIG. 14 illustrates a flow diagram in accordance with an embodiment for intelligent multi-scale image parsing. A method is provided for intelligent multi-scale image parsing. The method provided by this embodiment trains an artificial agent using a set of training images and applies the artificial agent to identify a landmark in a test image. The method is implemented by the system of FIG. 13 (discussed below) and/or a different system. Additional, different or fewer acts may be provided. For example, act B1409 may be omitted. The method is provided in the order shown. Other orders may be provided and/or acts may be repeated.

In act B1401, a state space of an artificial agent is specified for discrete portions of a training image. The state space is specified by both a parametric space and a scale space for the discrete portions of the training image. The state space has a length, width and depth expressed as a number of voxels defined by the parametric space, with a focal point defined as the center coordinate of the set of voxels. The resolution of the state space is specified by the scale space. For example, in each resolution, the state space may include the same number of voxels. However, at a higher resolution, the voxels are sampled from a smaller volume (greater density) of the image data. Conversely, at a lower resolution, the voxels are samples from a larger volume (lesser density) of the image data.

In act B1403, a set of actions are determined. The set of actions includes parametric actions specifying a possible change in the parametric space with respect to the training image and scale actions specifying a possible change in the scale space with respect to the training image. The parametric actions change the parametric space of the state space by sampling voxels from a different location in the image. For example, the parametric actions may be defined as any possible incremental changes in position of the state space that can be made by the artificial agent. The parametric actions may be defined as movements of the state space position one voxel in each direction that the agent may select from the set of upward, downward, left, right, forward, and backwards with respect to the training image. As such, the parametric actions change the focal point defined as the center coordinate of the set of voxels of the state space. The parametric actions may also include an action in which parametric space remains in the same position without movement.

The scale actions change the scale space of the state space. For example, the scale actions may be defined as any possible incremental changes in resolution of the state space that can be made by the artificial agent, such as by increasing or decreasing the resolution of the state space with respect to the training image. The scale actions may be defined as changing the volume or density of the image data for sampling voxels for the state space. The scale actions may also include an action in which scale space remains unchanged. As such, the set of actions includes an action in which the state space is unchanged.

In act B1405, a reward system is established based on applying each action of the set of actions and based on at least one target location of the training image. A reward value is determined for each possible selection of an action by the agent from the set of actions. The reward value is determined by the proximity of the current state space of the agent to the target location (e.g., landmark state). For example, the target location is an anatomical landmark location defined by position parameters of the landmark anatomical landmark. Thus, the reward value for each action is indicative of a proximity of the state space to the at least one target location after the action is performed.

In act B1407, the artificial agent learns an optimal action-value function approximator specifying the behavior of the artificial agent. The optimal action-value function approximator is parameterized using a deep neural network. Learning the optimal action-value function approximator maximizes a cumulative future reward value of the reward system based on sequences of actions performed by the artificial agent. For example, the behavior of the artificial agent is a sequence of actions moving the agent towards the target location of the training image, including parametric actions and scale actions. Parametric actions move the artificial agent towards the target location within a particular scale, and scale actions increase the resolution of the artificial agent. Learning by the artificial agent includes optimizing the action-value function using an episodic trajectory for the training image based on discrete portions of the training image via moving the state space. The episodic trajectory is indicative of a series actions that are performed by the artificial agent. Further, learning the optimal action-value function approximator also includes generating an experience memory database that includes a predefined number of previously evaluated state spaces for the training image. Learning the optimal action-value function approximator further includes sampling the experience memory database and updating parameters of the optimal action-value function approximator based on the experience memory.

In act B1409, the learned artificial agent is applied to a test image to automatically parse image content of the test image for a landmark location. Applying the learned artificial agent includes evaluating the optimal action-value function approximator for a current state space. The learned agent simultaneously obtains the optimal action-value function approximator for all possible actions at each current state space and applies a reward policy of the optimal action-value function approximator. For example, applying the reward policy of the optimal action-value function approximator includes determining a next action of the artificial agent based on balancing maximization of the cumulative future reward value by actions changing the parametric space and actions changing the scale space.

Figure 15:
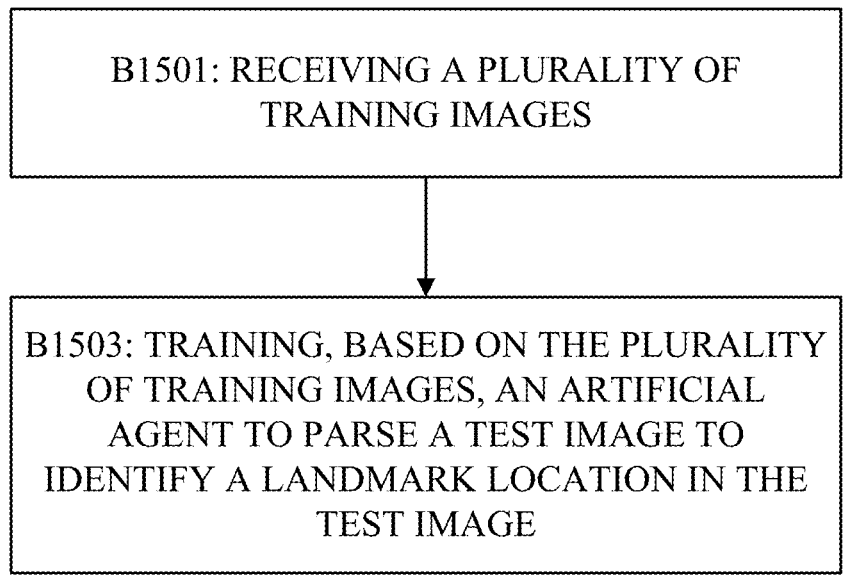
FIG. 15 illustrates a flow diagram in accordance with another embodiment of machine learning for intelligent multi-scale image parsing.

FIG. 15 illustrates a flow diagram in accordance with another embodiment of machine learning for intelligent multi-scale image parsing. A method of machine learning for intelligent multi-scale image parsing is provided. The method provided by this embodiment trains an artificial agent to identify a landmark using a set of training images. The method is implemented by the system of FIG. 13 (discussed below) and/or a different system. Additional, different, or fewer acts may be provided. For example, additional acts for applying the trained artificial agent may be included, such as landmark identification during image-based guidance applications in the operating room. The method is provided in the order shown. Other orders may be provided and/or acts may be repeated.

In act B1501, a plurality of training images are received. For example, the training images are three-dimensional medical images (e.g., CT, MR, Ultrasound, PET-CT, MR-PET, etc.). Each training image is annotated with a landmark location indexed in the image data. The training images provide ground truth data for the machine learning.

In act B1503, an artificial agent is trained, based on the plurality of training images, to parse a test image to identify a landmark location in the test image. Training the artificial agent simultaneously trains both an appearance model and a search strategy model. The appearance model is trained to identify the landmark location in a patch of the test image based on an annotated landmark location indexed in each of the training images. The search strategy model includes an optimal action-value function trained to search for the landmark location by parsing the test image through performing a series of actions. Additionally, training the search strategy model may include maximizing a future reward using a reward system of the optimal action-value function, and is based on reward values for each position and scale change of the patch. Simultaneously training the search strategy model and the appearance model may include encoding parameters of search strategy model and parameters of the appearance model in a multilayer data representation, such as a deep neural network. Further, training the artificial agent may include using experience memory from previously parsed patches at different scales to solve for parameters of the deep neural network.

The series of actions performed by the artificial agent changes the position and scale of a patch of the test image in order to parse the test image without performing an exhaustive search of the entire test image. Thus, the parsing searches less than the entire test image. As the artificial agent iteratively searches for a landmark in different scales, the artificial agent searches for the landmark location by changing the position of the patch at a first scale, by changing the patch scale from the first scale to a second scale, and then changing the position of the patch at the second scale. In an example, the convergence point at a previous scale is used as a starting point at a subsequent scale. Other combinations of actions may be performed.

Figure 16:
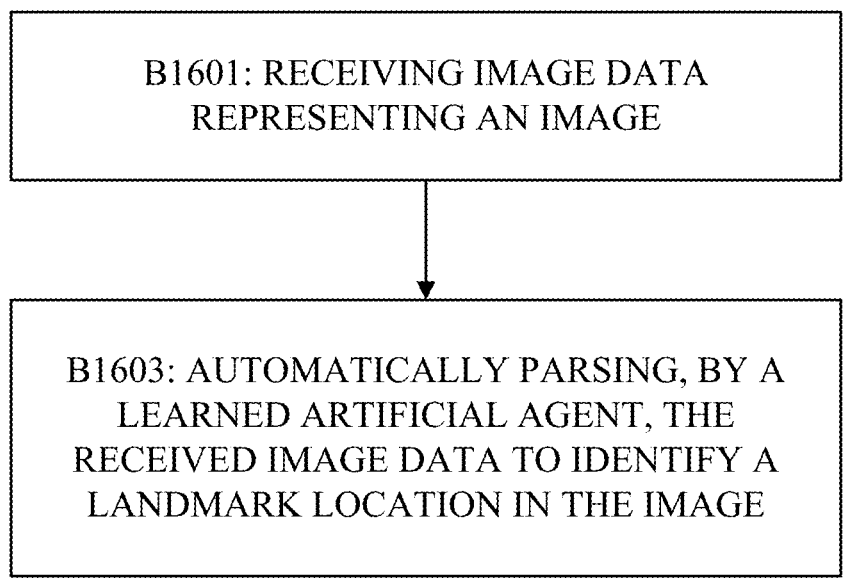
FIG. 16 illustrates a flow diagram in accordance with an embodiment intelligent multi-scale landmark identification in an image.

FIG. 16 illustrates a flow diagram in accordance with an embodiment intelligent multi-scale landmark identification in an image. A method for intelligent multi-scale landmark identification in an image is provided. The method provided by this embodiment uses a trained artificial agent to identify a landmark in captured or received image data, such as during image-based guidance applications in the operating room. The method is implemented by the system of FIG. 13 (discussed below) and/or a different system. Additional, different, or fewer acts may be provided. For example, additional acts for training the artificial agent may be included. The method is provided in the order shown. Other orders may be provided and/or acts may be repeated.

In act B1601, image data representing the image is received. In act B1603, a learned artificial agent automatically parses the received image data to identify a landmark location in the image. For example, the learned agent includes an optimal action-value function, and the learned artificial agent is configured to parameterize a patch of the image data in a trained hierarchical data representation. For example, the hierarchical data representation is a deep neural network. The hierarchical data representation is trained by maximizing a future reward of a reward system of the action-value function for each a plurality of available actions to reposition the patch of the image.

The learned artificial agent is also configured to determine a sequence of actions from the plurality of available actions to reposition and to rescale the patch based on the parameterized patch of the image data. The learned artificial agent is further configured to identify the landmark location in the repositioned and rescaled patch of the image. For example, automatically parsing the received image data includes performing the sequence of actions to move a location of the patch toward a location of a target patch and to increase the resolution of the patch. In an example, the sequence of actions comprises repositioning the patch in an upward, downward, left, right, forward, or backward direction in the received image and/or rescaling the patch to increase the resolution of the patch. The target patch includes the landmark location in the image, and the sequence of actions comprises a path converging on the landmark location by parsing less than the entire image. By varying the scale, less processing is performed to locate the landmark. The scale variation may avoid using some voxels. Further, determining the sequence of actions may include parameterizing at least one previous patch in the hierarchical data representation after repositioning and rescaling the patch.

Detailed description of various techniques employed by the disclosed embodiments depicted above and in FIGS. 9-12 and 14-16 are discussed below.

State Space

A state space is modeled as a candidate position for the landmark target and a fixed region around the candidate position. For example, a state space for a two-dimensional medical image application may be a square window (i.e., square patch) with a defined width and length in pixels. The candidate position for the state space is the coordinate point in the center of the square. Evaluation of a state space is an evaluation for the candidate position, representing a focal point of the agent.

A state space is defined by parameters of height and width of 60×60 pixels. A state space defined as additional or different parameters and may be generalized to any kind of parametric space. Other parameters defining a state space may include location, or rotation. Image data may have a margin, or pixel border (e.g., 30-pixel wide black margin for use with 60×60 pixel patch) so that the center of the moving window can effectively reach the edge of the image.

The artificial agent evaluates image data, selectively observes and evaluates the image data defined by the agent's current state space with respect to the image data. The agent's subsequent behavior for the candidate position is responsive to what is observed within the state space. A state space needs to be discriminative in order to limit the amount of data, minimizing computational load of the evaluation (rather than analyzing the entire image data set). The state space is self-describing based on its parameters to provide a context for the evaluation of image data at the current position of the state space. The state space is composed of parameters that are used to establish a focal point (e.g., one particular coordinate, pixel, or voxel), while also permitting limited perception of the surrounding context (state space dimension in a size and shape such as a pixel, or voxel). Similar to animal and human visual perception systems, dense local information is captured around a focal point and limited global context associated from the surrounding neighborhood is acquired without acquiring all available global information.

A locality assumption is made and a state observed at time t as $s_t=(I_t, x_t, y_t, l_t)$, i.e., a local patch of size $l_t \times l_t$ centered at position $(x_t, y_t)$ in the observed image $I_t$. States which are close to the target landmark location will directly capture the position of the landmark in their context. For distant states, the relation to the landmark location is intrinsic, captured indirectly by information from the context of the current patch.

Set of Actions

In each state space, the agent interacts with the enclosed environment of an image by selecting and performing actions from a pre-defined set of actions. The set of actions is chosen in such a way that the agent is given the possibility to explore the entire environment. Located in state $s_t$ at time t, (for a visual goal of identifying the location of a target landmark), the agent may a set of actions may be defined as the discrete actions of changing the position of the focal point of the state space by one pixel in a direction specified as: upwards, downwards, left, or right with respect to the training or test image. An action set may be defined to include an action that permits the agent to select non-action, staying at the same position. Each action is simplified to a single pixel move: $x_{t+1} \leftarrow x_t \pm 1$ and $y_{t+1} \leftarrow y_t \pm 1$. Once the target has been reached, no further action is performed, and the search is finished. Additional or alternative actions may include rotation around an axis, movement of multiple pixels in each action, and/or scaling. Actions may include multiple discrete steps and/or may occur simultaneously. Choices of action set may be selected that are not optimal. However, limitation of the action set is not limiting to the embodied method, as the present action set permits iteration and exploration of the entire content of the image.

Figure 20:
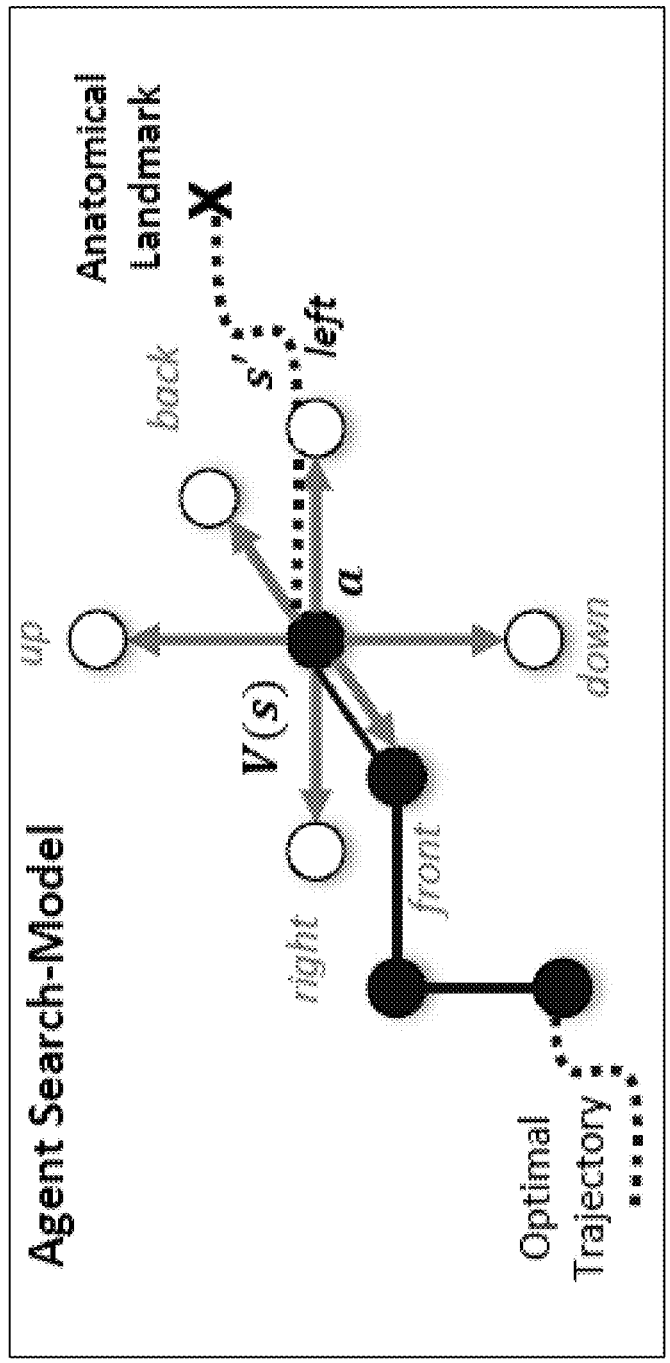
FIG. 20 illustrates a decision-based search strategy model according to an embodiment for intelligent multi-scale landmark identification.

In a three-dimensional state space, the agent may have a set of actions defined as the discrete actions of changing the position of the focal point of the state space by one voxel in a direction specified as: upwards, downwards, left, right, front and back with respect to the training or test image. Referring to FIG. 20, a schematic visualization of the decision-based search strategy model in state s is provided. In this embodiment the six possible actions allow for voxel-wise movement in the volumetric image space. As depicted in FIG. 20, the optimal decision with respect to the cumulative future reward is going left to state s'. The dashed line represents the optimal search-trajectory to the anatomical landmark X and the while the circles signify adjacent or neighboring voxels available for discrete voxel-wise navigation.

Rewards

The reward system is based on the change in relative position at state $s_t$ $(x_t, y_t)$ with respect to the target position of the landmark $s_{target}$:$(x_{target}, y_{target})$. Intuitively, for a move in the correct direction, a positive reward proportional to the target-distance reduction is given, whereas a move in the wrong direction is punished by a negative reward of equal magnitude. The reward at time t is given by Equation 7:

$$r_t = \text{dist}(s_t, s_{target}) - \text{dist}(s_{t+1}, s_{targ}) \quad \text{Eq. 7}$$

Exceptions to this rule may be additionally provided. For example, in one embodiment, the only exception to this rule is an attempt to leave the image field by crossing the image border. This action is always given the highest punishment of −1. The reward is correlated to the goodness of a performed action, providing a complex trial-error system, simulating the human experience more closely. Good actions, contribute significantly towards reaching the goal, are given a high reward, whereas actions that only marginally improve the state of the agent, receive little reward. This reward system is more complex compared to a simple +1 reward used in some conventional methods.

Rewards increase in or decrease based on distance to target position. Changes in accumulated rewards provide reinforcement learning for the agent to quantify its moves.

Deep Reinforcement Learning

The disclosed embodiments include both DL and RL, to provide a system using deep reinforcement learning. Given the state space, set of actions, and reward system, the goal of the agent is to learn how to identify the location of an anatomical landmark in a set of image data and to also automate the optimization of a method for efficiently identifying the anatomical landmark. That is, the agent, during training, both learns to identify the location of an anatomical landmark and determines a method to select the actions needed to traverse the image data in order to successfully identify the anatomical landmark (e.g., the agent determines a method for using) select actions and simultaneously itself for feature extraction by repeatedly interacting with the enclosed environment in order to maximize cumulative future reward (see, Eq. 4). This optimal behavior is defined by the optimal policy $\pi^*$ selected from the space of all possible policies $\pi \leftarrow p(\text{action}|\text{state})$. As in Equation 5, the agent develops its own optimal policy for a training data set based on the optimal action-value function $Q^*$.

The disclosed embodiments are model-free, temporal difference approaches that use a deep convolutional neural network (CNN) to approximate the optimal action-value function $Q^*$. The parameters of a deep CNN may be defined as $\theta = [\vec{\omega}, \vec{b}]$, where $\vec{\omega}$ represents the weights of the network, and $\vec{b}$ defines the biases of the neurons. This architecture is used as a generic, non-linear function that approximates $Q(s, a; \theta) \approx (s, a)$, called deep Q network (DQN). Reference update-delay and experience replay are used to account for possible divergence issues during training.

Figure 8A:
FIG. 8A-8D are visualizations of optimal action-value function approximations and corresponding images in accordance with disclosed embodiments.
Figure 8A:
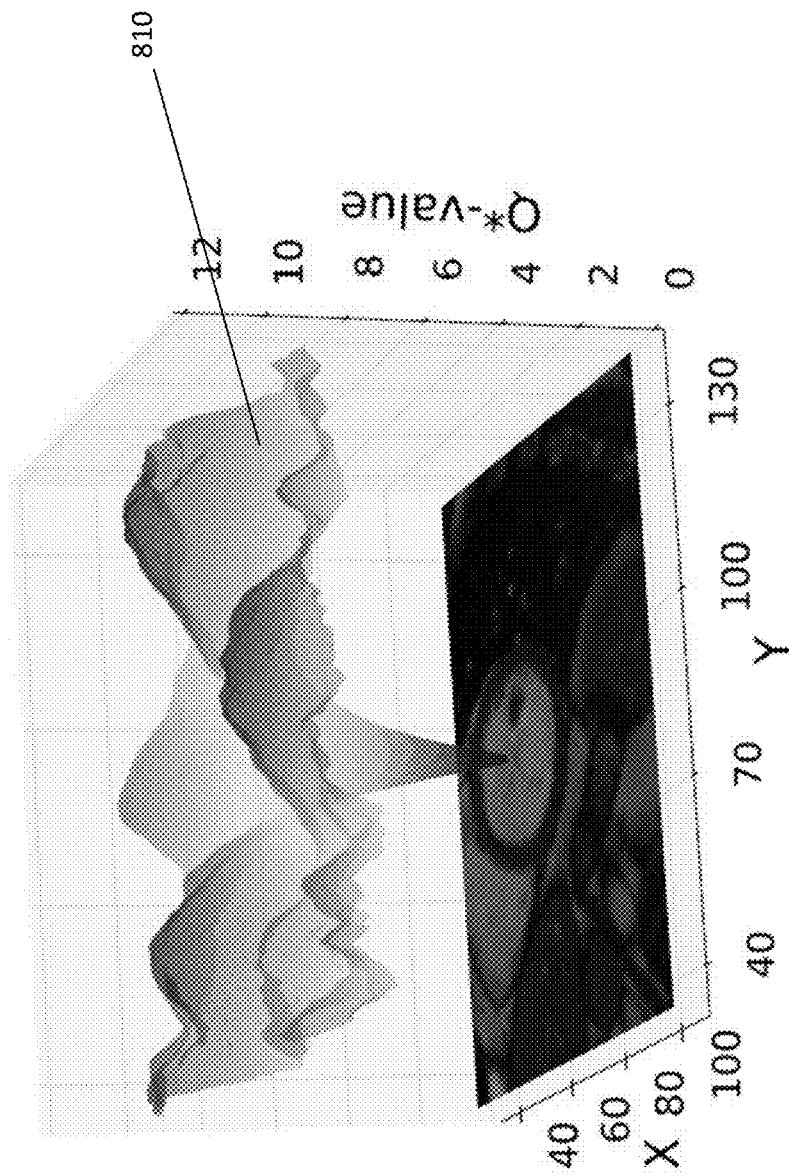
Figure 8B:
Figure 8B:
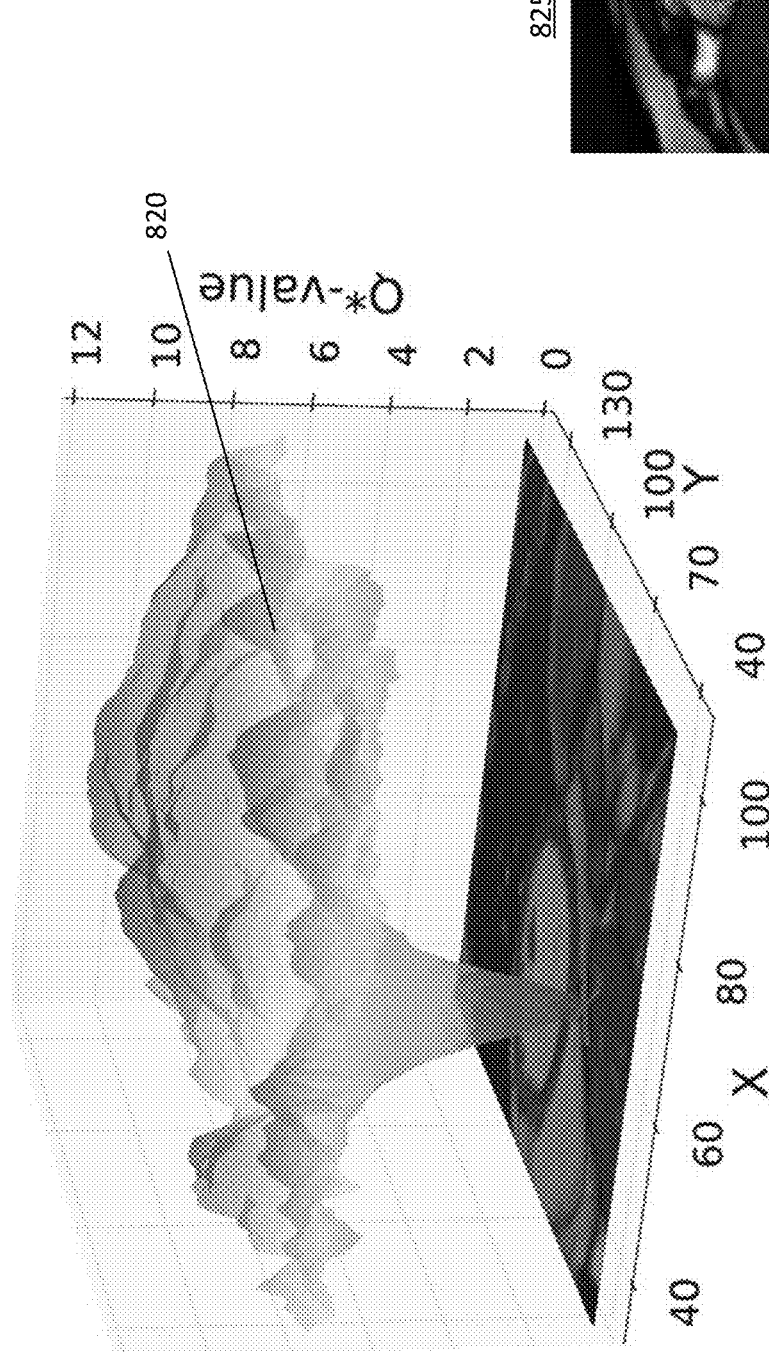
Figure 8C:
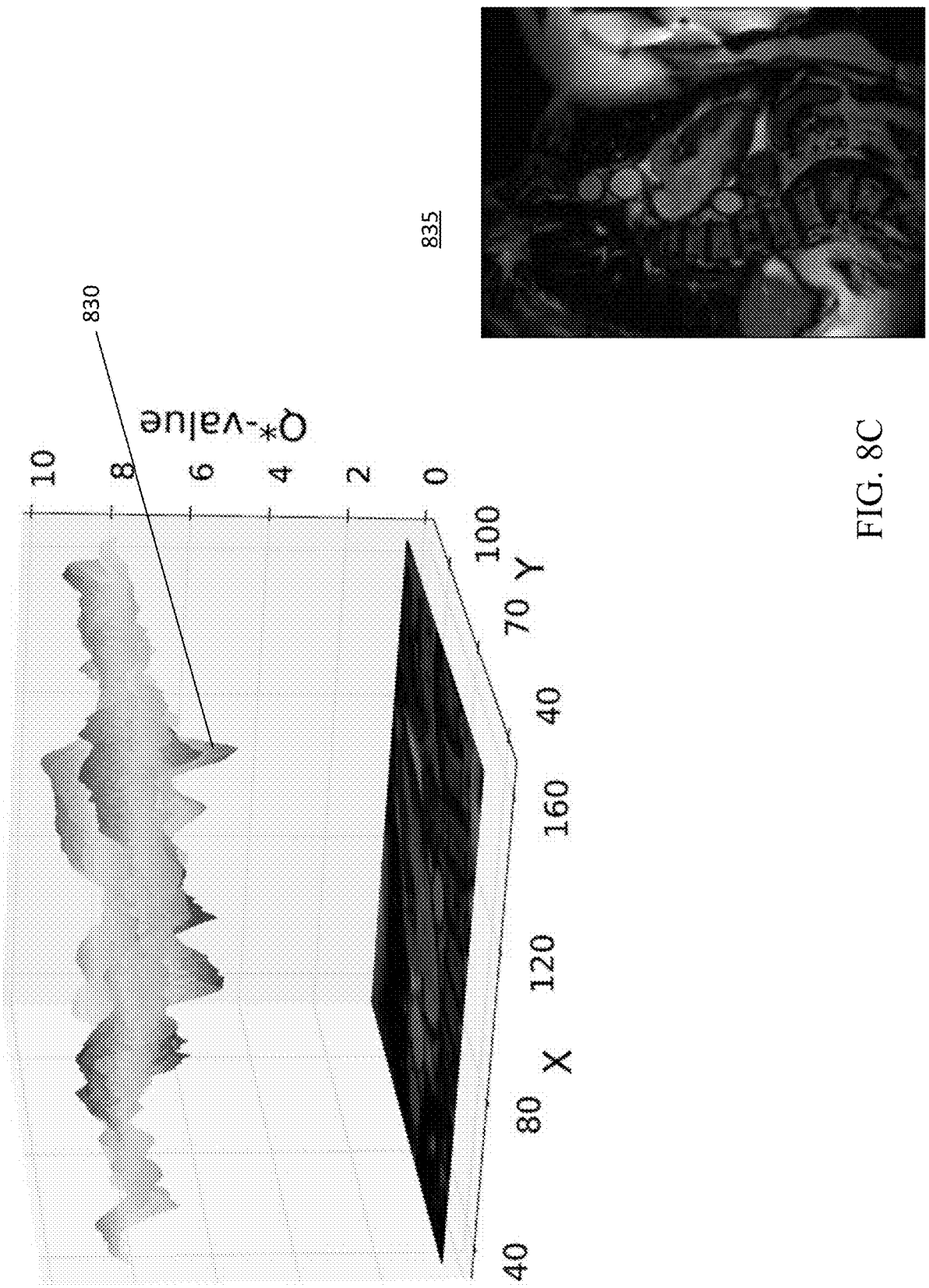
Figure 8D:
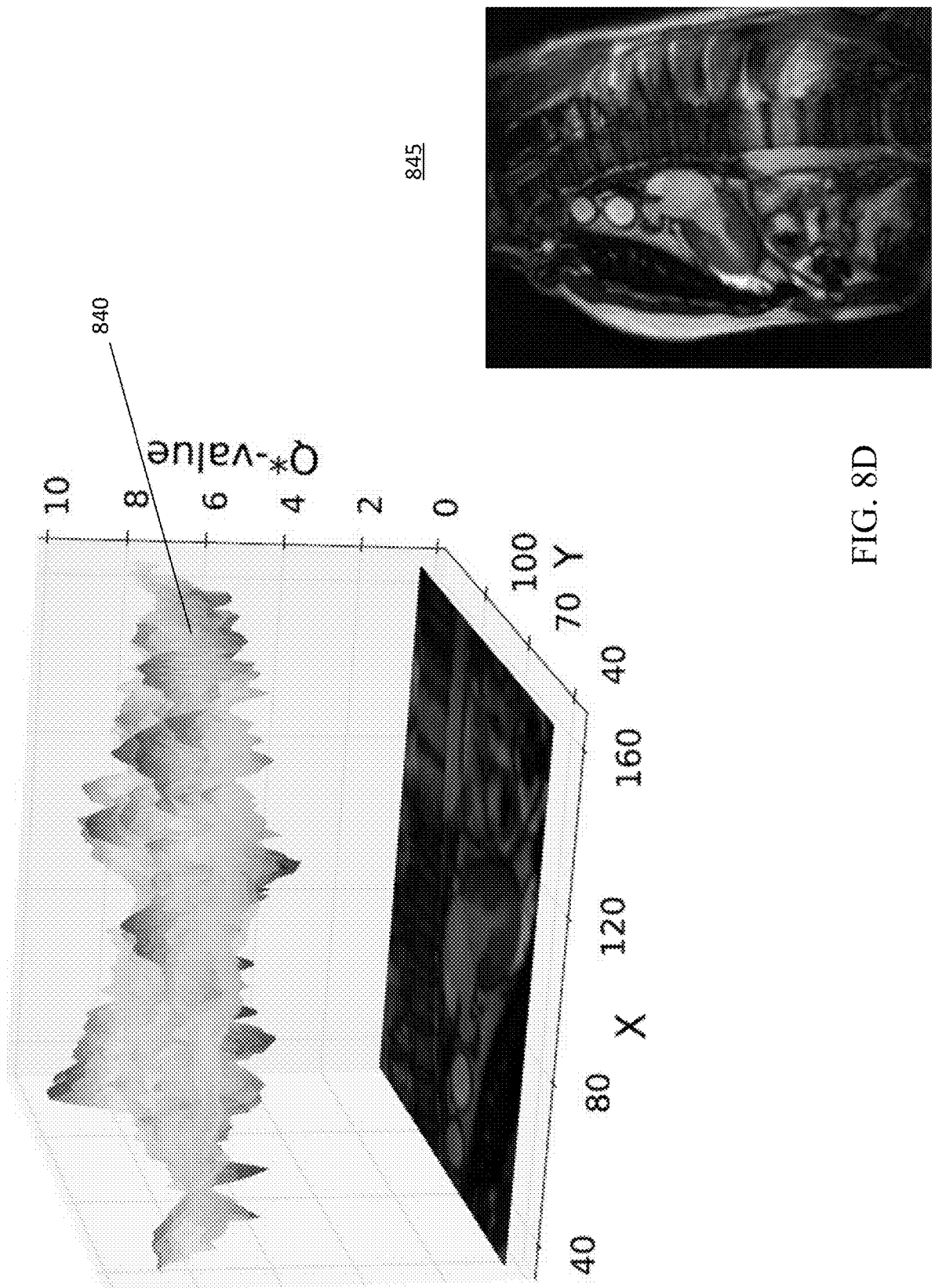

Visualization of the optimal action-value function $Q^*$ are depicted in FIGS. 8A-8D. Visualizations 810, 820, 830 and 840 are $Q^*$-fields indicating the highest expected reward considering all actions allowed in that state space (i.e., the highest expected reward for the center point of each possible position of the state space) for images 815, 825, 835, and 845. FIGS. 8A and 8B illustrate convergence at the LV-center and the posterior RV-insertion point corresponding to the landmarks of FIG. 3A. Convergence is illustrated as the global minimum point reaches near zero-values at the location of the target landmark, depicted as an X on the projected MR image. The $Q^*$-fields of FIGS. 3C and 3D are also representative of target landmark goals for the LV-center and posterior RV-insertion point, respectively. However, images 835 and 845 do not contain the target landmark, so the $Q^*$-fields do not approach zero at any point in the images.

Similar to the temporal difference Q-Learning algorithm, a deep Q network can be trained in a reinforcement learning setup using an iterative approach to minimize the mean squared error based on the Bellman optimality criterion as in Eq. 6. At any iteration i, the optimal expected target values can be approximated using a set of reference parameters $\theta_i^{ref} := \theta_j$ from a previous iteration j<i provided in Equation 8:

$$y = r + \gamma \max_{a'} Q(s', a'; \theta_i^{ref}) \quad \text{Eq. 8}$$

A sequence of well-defined optimization problems drives the evolution of the network parameters. The function at each step i is defined as Equation 9:

$$\theta = \min_{\theta_i} \mathbb{E}_{s,a,r,s'}[(y - Q(s, a; \theta_i))^2] + \mathbb{E}_{s,a,r}[\mathbb{V}_{s'}[y]] \quad \text{Eq. 9}$$

This supervised setup for deep learning combines a mini-batch gradient-based approach with back propagation. Stochastic gradient descent steps are periodically applied, approximating the gradient by randomly sampling the gradient function, given as Equation 10:

$$\nabla_{\theta_i} Err(\theta_i) = \mathbb{E}_{s,a,r,s'}[(y - Q(s, a; \theta_i))\nabla_{\theta_i} Q(s, a; \theta_i)] \quad \text{Eq. 10}$$

where $Err(\theta_i)$ represents the error function introduced in Equation 9.

At the beginning of training, the agent freely navigates through the space at random. That is, no operator or user input is required. Instead, gradually during training, the agent learns a policy, which tells the agent what is correct. Initial test images used for training require pre-marked annotations identifying x,y ground truth (e.g., the target landmark).

Reference Update-Delay

Use of a different network to compute the reference values for training provides robustness to the algorithm. Changes to the current parameters $\theta_i$ and implicitly to the current approximator $Q(\bullet; \theta_i)$ cannot directly impact the reference output y, introducing update-delay and thereby reducing the probability to diverge obsolete and suboptimal regions of the optimization space.

FIG. 2, is a more in-depth visualization of the main system diagram introduced in FIG. 1. In a given state, specified by the current view patch, the neural network is evaluated on that particular patch to simultaneously obtain $Q^*$ value estimates for all possible actions: $Q(s, a_1)$, $Q^*(s, a_2)$, . . . . Given the estimates, the agent applies E-greedy policy, choosing a random action with probability E and following the current policy estimation (choosing the action with the next future, discounted reward) with probability 1-E. During learning, a value decay is applied on the parameter E reaching a trade-off between an effective space exploration in a greedy, consistent policy exploitation strategy.

Experience Replay

Frequent updates of the parameters to the optimal action-value function approximator facilitates more efficient artificial agent training. Experience replay may be used in some embodiments. In this experience replay, the agent stores a limited amount of previously visited states (e.g., the last dates), the so-called experience memory, and then samples that memory to update the parameters of the underlying neural network. Learning takes place in a sequence of episodes that quantify the local performance of the agent on given training images. Before the start of one episode, the agent is given a random image from the complete training set at any random start state, e. g., start position in that image. During the course of the episode, the agent performs actions applying the ∈-greedy behavior policy navigating through this local environment (the given training image). The episode finishes when the target state is reached, in other words the landmark location is found, or a predefined maximum number of actions are executed. A target state may be an anatomical landmark, an anatomical object, a region, point, area, or volume. The target state may be a comprehensive template of measurements from image parsing and the set of actions may include changes of the parameters available to product the optimal set of measurements. This defines a so-called trajectory $t_i$ (also called episodic trajectory) in image space that includes the applied search strategy as a sequence of visited states. These trajectories are stored in replay memory, representing the entire experience the agent has accumulated on different images. In some embodiments, the last P trajectories are stored as $E=[t_2, \ldots, t_p]$. At fixed intervals during training (e.g., every 4-6 state transitions), a perimeter update is performed using a random mini-batch of states extracted from E. This approach achieves the goal of ensuring training convergence. Updating the deep neural network on locally correlated states (similar to Q-learning) does not generalize. Instead, performance of the network in other parts of the state space are strongly affected. Using a uniformly sampled set of previous experiences, averages the distribution of the network input, and reducing oscillations ensure a faster and robust learning experience.

Scale Space

A scale space may be modeled for the state space. For example, a three-dimensional discrete image signal is defined as: $I: Z^3 \to R$. A continuous scale-space of the image signal is defined as:

$$L(x; t) = \sum_{\xi \in Z^3} T(\xi; t) I(x - \xi),$$  Eq. 12 where $t \in R_+$ denotes the continuous scale-level, $x \in Z^3$, $L(x; 0) = I(x)$ and T defines a one-parameter family of kernels.

The scale-space signal representation in high-dimensional N-D space provides no enhancement of local extrema, and implicitly causality of structure across scales. Several conditions enforced on the scale-space kernels T, especially the semi-group structure, provides that the scale-space representation L satisfies the differential equation:

$$\partial_t L = A_{ScSp} L,$$  Eq. 13 where $A_{ScSp}$ is an infinitesimal scale-space generator based on discrete approximations of the Laplace operator, enabling learning in the scale-space.

Using the scale-space, the optimal action-value function Q* may be redefined based on a scale-space representation of the input image I. The state-representation s and model parameters θ on the scale-space L and the current scale-level t define that:

$$Q^*(s, a \mid L, t) = E_{s'}\left(r + \gamma \max_{a'} Q^*(s', a' \mid L, t')\right),$$  Eq. 14 where $t' \in R_+$ represents the scale-level after executing action a. Thus, the object search occurs in continuous image scale-space allowing the system to exploit structures on different scales, capturing global context and gain robustness. Because the image dimensionality is preserved across scales, a trade-off between sampling efficiency and global context is made. In addition, because the scale-space parameter $t' \in R_+$ is continuous and the model parameters θ depend on the scale, a learning model captures the variability in image space and the variability in scale-space. To avoid complexity, a discrete approximation of the continuous scale-space L is defined as:

$$L_d(t) = \Psi_\rho(\sigma(t) * L_d(t+1)),$$  Eq. 15 where $t \in N_0$ denotes the discrete scale-level, σ represents a scale-dependent Gaussian-like smoothing function and $\Psi_\rho$ denotes a signal operator reducing the spatial resolution with factor ρ using down-sampling. Down-sampling the signal may introduce aliasing effects, however the aliasing effects do not affect the learning process, enabling the system state to capture global context on coarse resolution while maintaining the sampling complexity.

Multi-Scale Deep Reinforcement Learning

Deep reinforcement Q-learning, using the deep Q network (DQN) discussed above, may be extended to include multi-scale data analysis for anatomical landmark detection, referred to as Multi-Scale Deep Reinforcement Learning (MSDRL). The search strategy utilized by MSDRL determines the optimal size or density of each observation made by the artificial agent at a given point in time while searching for the anatomical landmark. For example, at the artificial agent begins searching image data with a coarse field-of-view or density and iteratively decreases the field-of-view or density to locate the anatomical landmark. For example, the coarse field-of-view provides greater context for the artificial agent to begin converging on the anatomical landmark. After searching at coarse field-of view, the artificial agent increases resolution to a finer field-of-view to analyze appearance factors to converge on the anatomical landmark. The coarse field-of-view focuses the finer field-of-view, avoiding finer examination at locations spaced from the landmark. During training, the artificial agent determines applicable context and appearance factors at each effective scale. In an example, independent search strategy models are used for each level of the scale-space to adapt the search to the most discriminative visible structures at each level.

Thus, using the concept of a scale-space, the artificial agent naturally varies the size of the field-of-view across scales to search for the anatomical landmark. The scale-space concept is similar to a natural focusing mechanism acquiring a global context at coarse scale while gradually focusing and constraining the attention and search-range when moving to finer scales. Incorporating the concept of a scale-space, the MSDRL may increase the efficiency and robustness of the artificial agent by searching across scales, increasing the ability of the artificial agent to perform comprehensive three-dimensional image parsing.

In an embodiment, the MSDRL search strategy is defined to include a discrete scale-space representation L of the image data. Defining the scale-space representation is equivalent to imposing a hierarchical structure on the state-space providing for a search policy at each scale: $S_n \supseteq S_{n-1} \supseteq \ldots \supseteq S_0$. The hierarchical structure of the scale space prevents the MSDRL from enhancing local extrema while parsing the image data, providing an advantage in the search strategy utilizing the scale-space. Thus, by non-enhancement of local extrema, no artificial structures or new image information appear in coarser scale-space representations of the image data. The scale-space representation is used to model a unified search policy it $\pi \in S_n$ conditioned on the scale-space L:

$$\pi \sim \max_a Q^*(s, a; L) \qquad \text{Eq. 11}$$

where (s, a) denotes the state-action pair and Q* defines the optimal action-value function (as discussed above regarding Deep Reinforcement Learning). For example, the unified search policy is modeled by adding additional actions that allow navigation in the selected scale-space starting from coarse to fine scale levels. In one embodiment, two additional actions are defined as scale-space actions: zoom-in and zoom-out. For three-dimensional image data, parametric-space actions are defined as: upward, downward, left, right, forward, and backward. Thus, in this example, the action-value function is defined to include six possible parametric-space actions and two possible scale-space actions. Alternatively, information from groups of image representations is fused from the scale-space for joint navigation on different scale levels.

Figure 17:
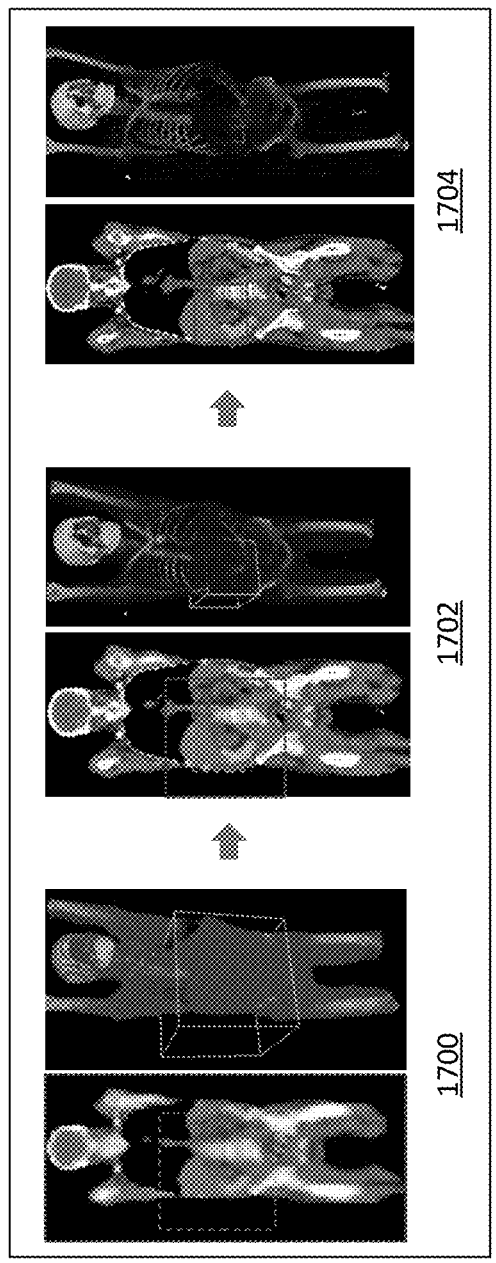
FIG. 17 illustrates a trajectory for training an artificial agent for landmark detection according to an embodiment of multi-scale deep reinforcement learning.

FIG. 17 illustrates a trajectory for training an artificial agent for landmark detection using multi-scale deep reinforcement learning. For example, FIG. 17 depicts detecting the center of the right kidney of a patient at three different scales. The system is trained in a hierarchical manner, starting from the coarsest scale (e.g., depicted as 1700, scale $s_0$ is set to 16 mm) to an intermediate scale (e.g., depicted as 1702, scale $s_1$ is set to 8 mm) to the finest scale (e.g., depicted as 1704, scale $s_2$ is set to 4 mm). The artificial agent is trained at each scale (as discussed above regarding Deep Reinforcement Learning). During training, the artificial agent learns context and appearance factors at each effective scale. For example, at the coarsest scale 1700, the artificial agent may be trained by performing a landmark search over the entire image. By training the artificial agent over the entire image, the artificial agent learns to quickly identify a relevant area in the image. The artificial agent is then trained at the finer scales 1702 and 1704, with the search area of the image bound by a ground-truth annotation $\vec{g}$ with the symmetric margin $\vec{b} = (\pm b_x, \pm b_y, \pm b_z)$ at each scale. The symmetric margin is selected such that the spatial search-window decreases at finer scales. For example, in 1702 and 1704, the search area is bound by the solid border signifying the search limits for the agent, and the dashed border represents the field-of-view of the agent (e.g. the state-space at a given scale). As depicted in FIG. 17, the search is bound only by image boundaries at the coarsest scale 1700 and gradually reduces from the intermediate scale 1702 to the finest scale 1704.

In an embodiment, multi-scale landmark detection with M levels is provided. Given a discrete scale-space definition $L_d$, a navigation model for each scale level is defined as:

$$\Theta = [\theta_0, \theta_1, \ldots, \bar{\theta}_{M-1}] \qquad \text{Eq. 16}$$

where M is the number of different scales. Low-level features can be shared across scales leading to a single multi-scale search model. However, training a different model on each scale yields optimal results. Across scales, all meta-parameters are cloned defining each model as:

$$Q(\cdot, \cdot; \theta_t | L_d, t), \forall t < M, \qquad \text{Eq. 17}$$

where the range of the state-representation is included (i.e., the size of the extracted box or patch). The search starts at the coarsest scale-level, M−1, with the search-model trained for convergence from any starting point in the image. On the coarsest scale-level, the field-of-view of the agent is very large acquiring sufficient global context to provide an effective navigation. Upon convergence the coarsest scale-level, the scale-level is changed to M−2 and the search continues from the convergence point for M−1. The same process is repeated on the following scales until convergence on the finest scale. In this embodiment, for each scale-level, except the coarsest scale-level M−1, the exploration range may be constrained based on the convergent behavior on higher scales. For example, referring to FIG. 22 (discussed below), the search-ranges for each scale-level are adapted during training.

Based on the definition of the discrete scale-space $L_d$ and the independent search models across scales, each scale-level, $0 \leq t < M$, is trained according to:

$$\hat{\theta}_t^{(i)} = \arg\min_{\theta_t^{(i)}} E_{s,a,r,s'}\left[(y - Q(s, a; \theta_t^{(i)} | L_d, t))^2\right], \qquad \text{Eq. 18}$$

with $i \in \mathbb{N}_0$ denoting the training iteration and the reference estimate y being determined using the update-delay as:

$$y = r + \gamma \max_{a'} Q(s', a'; \bar{\theta}_t^{(i)} | L_d, t) \qquad \text{Eq. 19}$$

Figure 22:
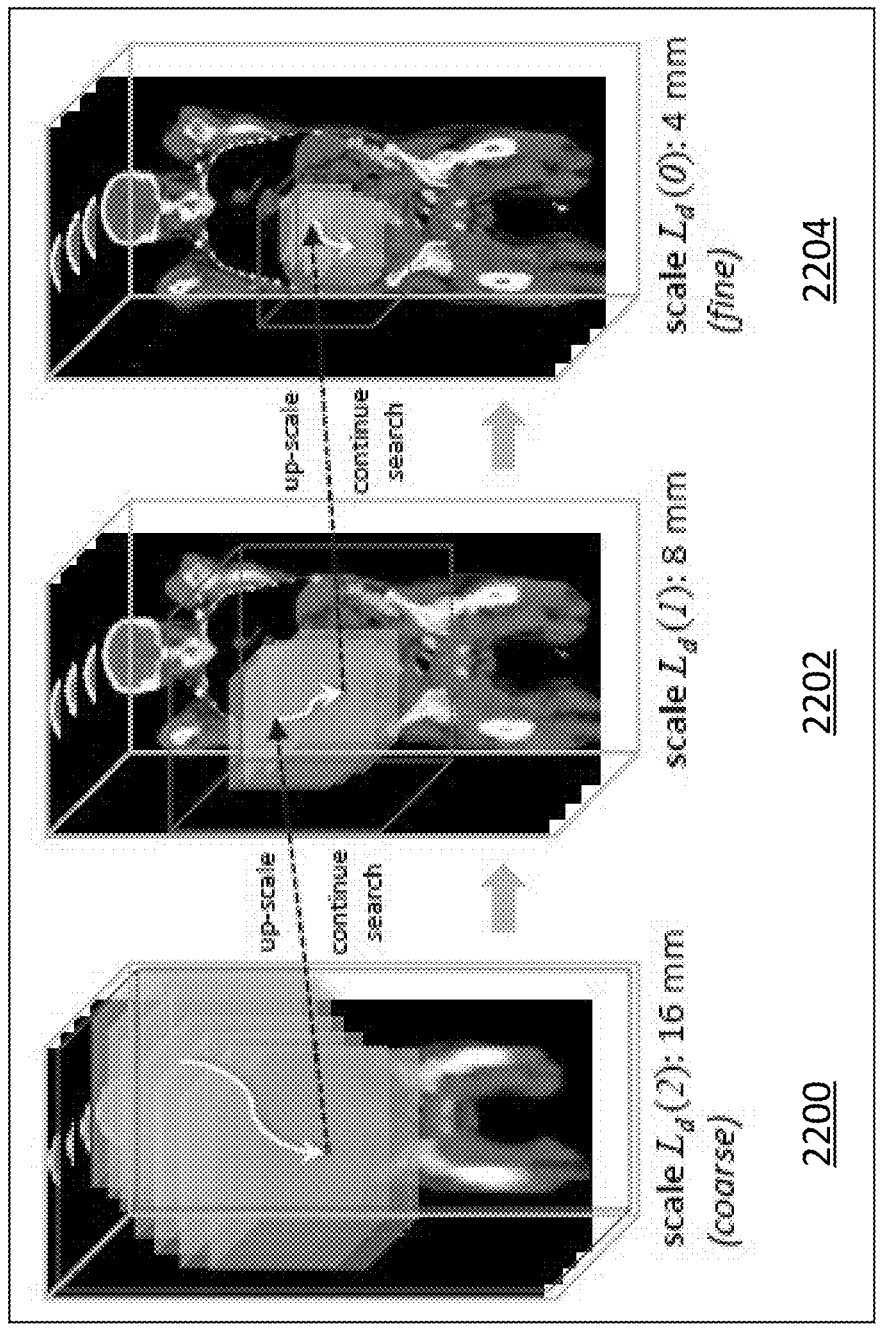
FIG. 22 illustrates a detection pipeline for the right kidney of a patient according to an embodiment.

FIG. 22 illustrates an example detection pipeline for the right kidney of a patient. In this example, the search starts at the average location of the right kidney in the training data on the coarsest scale-level $L_d(2)$. On each scale $L_d(k)$, where $k \geq 0$, the artificial agent navigates the image data until convergence at an oscillation-point of the trajectory between neighboring voxels. The convergence point at a previous scale-level $L_d(k)$ is used as starting point on the subsequent scale-level $L_d(k-1)$. The process continues at each of the following scale-levels with the convergence point on the finest scale marked as the detection result. The solid arrows depict the optimal three-dimensional search trajectories for each scale. Along each trajectory, a sequence of local environments is represented by the image information in the form of a three-dimensional box centered at the location of the agent encoding the state. A constrained region is sampled and explored during training on each of the scales, however on the coarsest scale, the region is constrained only by the entire three-dimensional volume. On subsequent scale-levels, the regions are adapted during training, decreasing with the spatial resolution at each scale.

According to this embodiment, the artificial agent may be trained using the following algorithm:

---

Algorithm 1 Training Multi-Scale DRL for Detection

---
1:    Given N training images: $I_1, I_2, \ldots, I_N$
2:    Define discrete scale-space: $L_d(t)|_{0 \leq t < M}$

| Algorithm 1 Training Multi-Scale DRL for Detection |
| --- |
| 3:   Initialize system memory: M(0, ... , M – 1) = [ ] |
| 4:   Initialize exploration factor: ϵ = 1.0 |
| 5:   while ϵ > 0.1 do |
| 6:      for all scale-levels 0 ≤ t < M do |
| 7:         Select random image and starting-point |
| 8:         Sample ϵ-greedy path T with Q(., .;θ$_t$ | L$_d$, t) |
| 9:         M(t) ← M(t) ∪ [T] |
| 10:        Train Q(., .;θ$_t$ | L$_d$, t) according to Equation 12 |
| 11:        Reduce search range on scales 0, ... , M – 2 |
| 12:     end for |
| 13:     Decay ϵ – reduce randomness |
| 14:  end while |
| 15:  Output Θ = [$\hat{θ}_0$, $\hat{θ}_1$, ... , $\hat{θ}_{M-1}$] – estimated models |

In another embodiment, the following parameters are used for training: agent field-of-view box is 25×25×25 pixels at each scale; search margin is ±10x±10y±10z pixels at each scale; number of episodes is 250; episode length is adaptive, starting at 1000 and decaying during learning; epsilon greedy learning with ε=1.0 initially; and the network architecture includes three strided-convolution layers with batch-normalization and three fully connected layers on top. In this embodiment, the training includes 250 episodes. For each episode, a random image is selected from a set of training images. For each scale s from coarsest to finest, a random initialization location is selected for trajectories within the boundaries $\vec{b}$ and the ε-greedy trajectory is sampled at scale s within boundaries $\vec{b}$. The sampled trajectory is stored in in experience memory at scale s. The policy is then trained at scale s using the acquired experience memory and ε is decayed.

Figure 18:
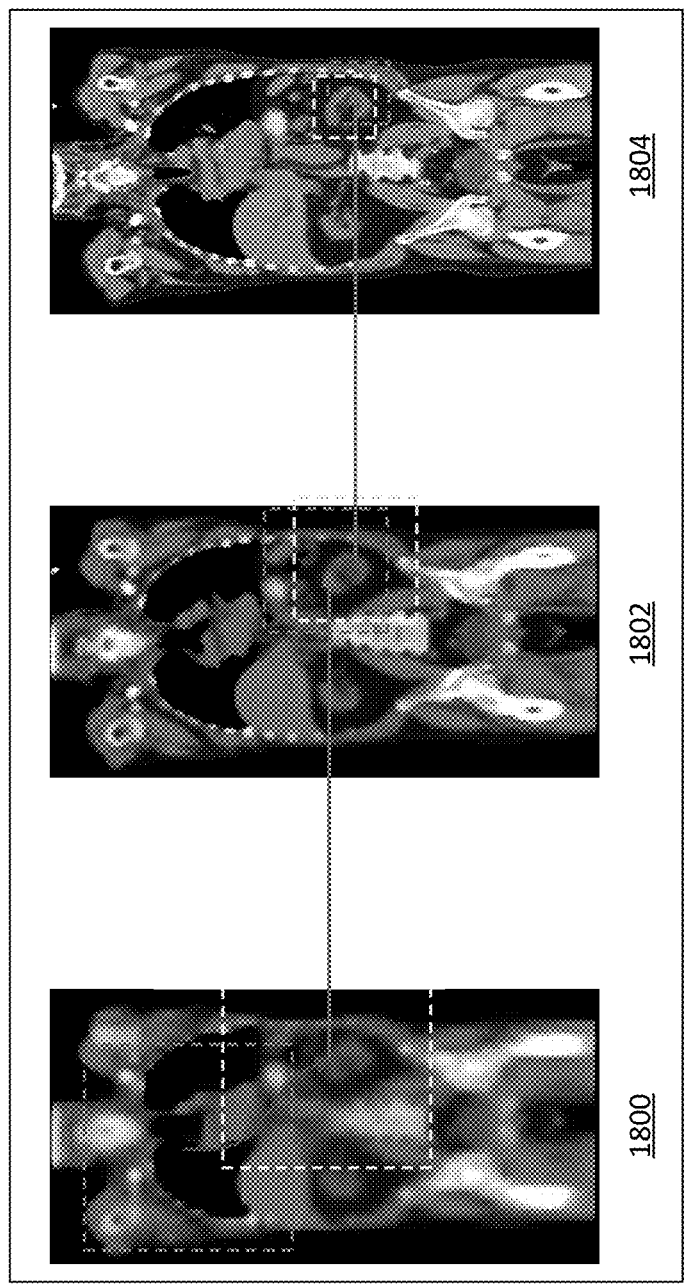
FIG. 18 illustrates a projection of a search trajectory according to an embodiment for intelligent multi-scale image parsing.

FIG. 18 illustrates a two-dimensional projection of a search trajectory of intelligent multi-scale image parsing. For example, FIG. 17 depicts a search trajectory for identifying the center of the left kidney of a patient using multiple scales. Although the visualization is projected in two-dimensions, the search trajectory is performed in three-dimensions. Using a trained artificial agent, the artificial agent parses the image data to identify the anatomical landmark (i.e., the left kidney). At 1800, the image is parsed at a coarse scale so with a search area of 16 mm. Using context derived from the image data, the artificial agent identifies a general area where the left kidney is located. As illustrated in 1800, the artificial agent uses the context of the image to move the search area from a starting point toward and converging on the left kidney. At 1802, the portion of the image found at 1800 is parsed at an intermediate scale $s_1$ with a search area of 8 mm. Using context and appearance derived from the image data, the artificial agent moves the search area from a starting location toward and converging on an area near the center of the left kidney. At 1804, the image is parsed at a fine scale $s_2$ with a search area of 4 mm. Using appearance derived from the image data, the artificial agent moves the search area from a starting location toward and converging the center of the left kidney. As such, at each scale, the artificial agent navigates the image from a starting location to a convergence location detecting the anatomical landmark at each scale. The arrows signify the search trajectory at each scale, indicating that the artificial agent parses less than the entire image by performing a non-exhaustive search. Further, the convergence point at one scale is used as the starting location or initialization point at the next finer scale.

Figure 21:
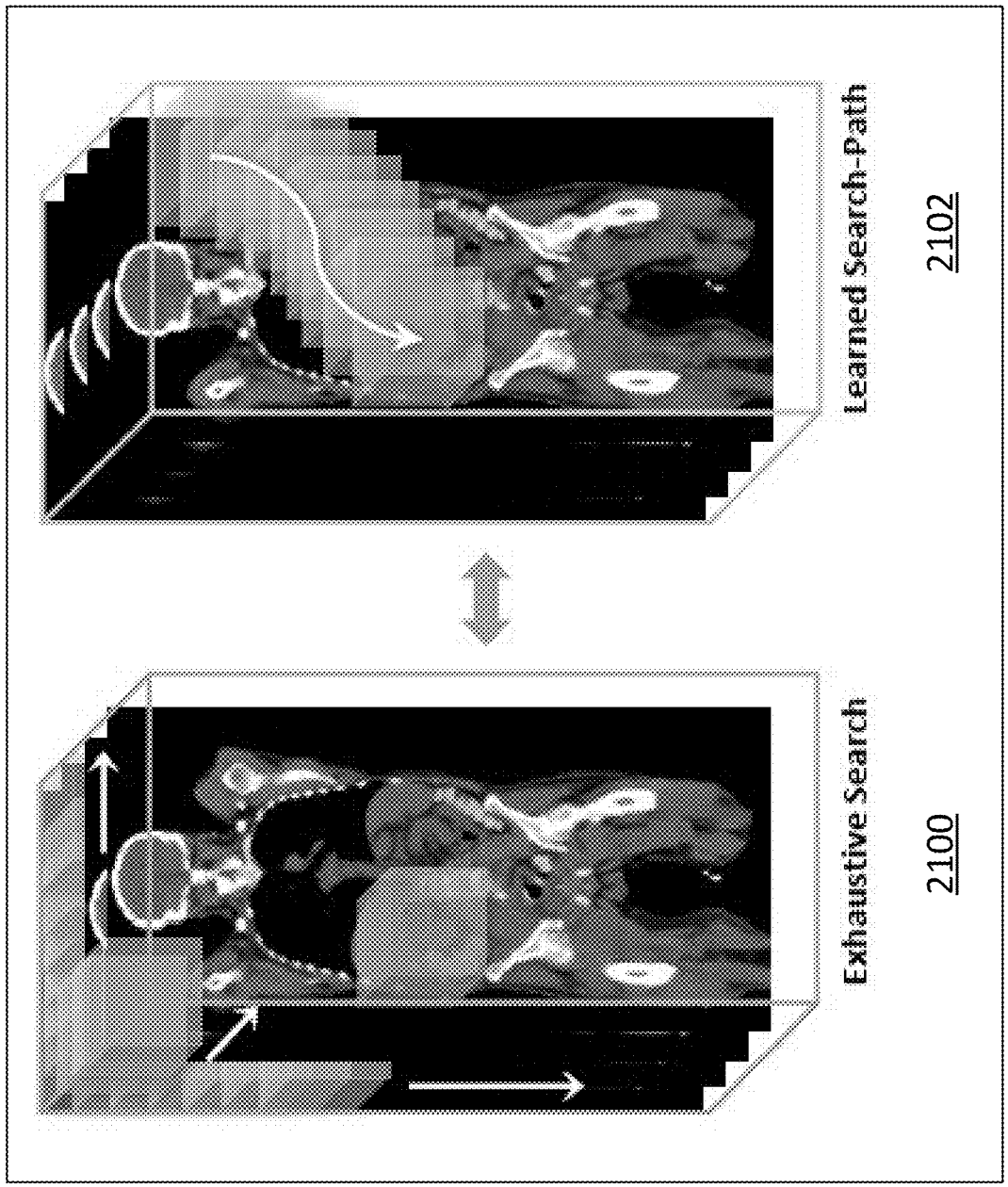
FIG. 21 illustrates differences between exhaustive scanning of prior systems and learned search-path scanning of intelligent multi-scale landmark detection.

Referring to FIG. 21, illustrates differences between exhaustive scanning of prior systems and learned search-path scanning intelligent multi-scale landmark detection. In 2100, a prior system based on exhaustive scanning is depicted. Prior systems typically test all hypotheses extracted from the volumetric input and then apply a form of aggregation and/or clustering of high-probability candidates to obtain a final result. In contrast, at 2102, learned search-path scanning learns the appearance of the anatomy and a strategy of how to find a target anatomical landmark. For example, the search-path scanning starts at any given point $\vec{P}_o$ in the image space and defines a three-dimensional trajectory in image space (depicted as a curve converging to the sought anatomical landmark location, such as the right kidney).

In an embodiment, a system test starts with the coarsest scale $s_0$ from a starting point P. In this example, the starting point P is the average location of the landmark in the training dataset. The trained agent performs a search at scale $s_0$ until convergence on the landmark. Convergence may be determined when the agent oscillates between neighboring voxels. The search continues by searching each scale (e.g., $s_1$, $s_2$ ... $s_n$) in a similar way on using the convergence point from the previous scale as starting point. As such, at each scale, the agent refines the landmark detection from the previous scale. In this embodiment, the testing includes setting the starting point P as average location from training set. Then, for each scale s from coarsest to finest, search from P until reaching a convergence point T and setting P as T for the next scale. The output is the location T at the finest scale.

As discussed above, the convergence point at a previous scale-level is used as starting point on the subsequent scale-level, and the search continues at each of the following scale-levels with the convergence point on the finest scale marked as the detection result. Further, the starting point $\vec{P}_o$ of a search is defined based on the expected relative position $\vec{r}$ of the anatomical landmark found using the training data set. Given N training volumes $I_1, I_2, \ldots , I_N$, $\vec{r}$ may be defined as:

$$\vec{r} \in [0, 1]^3 \text{ as } \forall d \in \{1, 2, 3\}, \qquad \text{Eq. 20}$$

$$\vec{r}(d) = \frac{1}{N}\sum_{k=1}^{N} \frac{\text{size}[I_k]_d}{\text{gtruth}[I_k]_d}, \qquad \text{Eq. 21}$$

where size $[I_k]$ and gtruth $[I_k]$ denote the size of the image $I_k$ and the ground-truth annotation of the object, respectively, and d is the dimension index (e.g., here three-dimensions).

Based on $\vec{r}$ we define the starting point as:

$$\vec{p}_o = \text{size}[I]\vec{r}. \qquad \text{Eq. 22}$$

Using this type of starting point as described may yield optimal results as opposed to starting from random locations in the volume.

Trajectory convergence is implicitly related to the general convergence properties of the system. Heuristic techniques, like memory replay, update-delay or random-exploration provide training stability and convergence. Trajectory convergence criteria may be defined, given a search-trajectory $T=[\vec{p}_0, \vec{p}_1, \ldots ]$, ∃k, k'∈$N_o$, with k'>k≥0, such that $\vec{P_k}=\vec{P_{k'}}$ with the length l=k'–k minimal. Trajectories converge on small, oscillatory-like cycles. Once such a cycle is identified, the search is concluded and the detected $\vec{P_k}$ is provided as a result. As discussed, the stopping criteria is robust, and trajectories may not converge to long cycles, where k'−k>>0.

Figure 23:
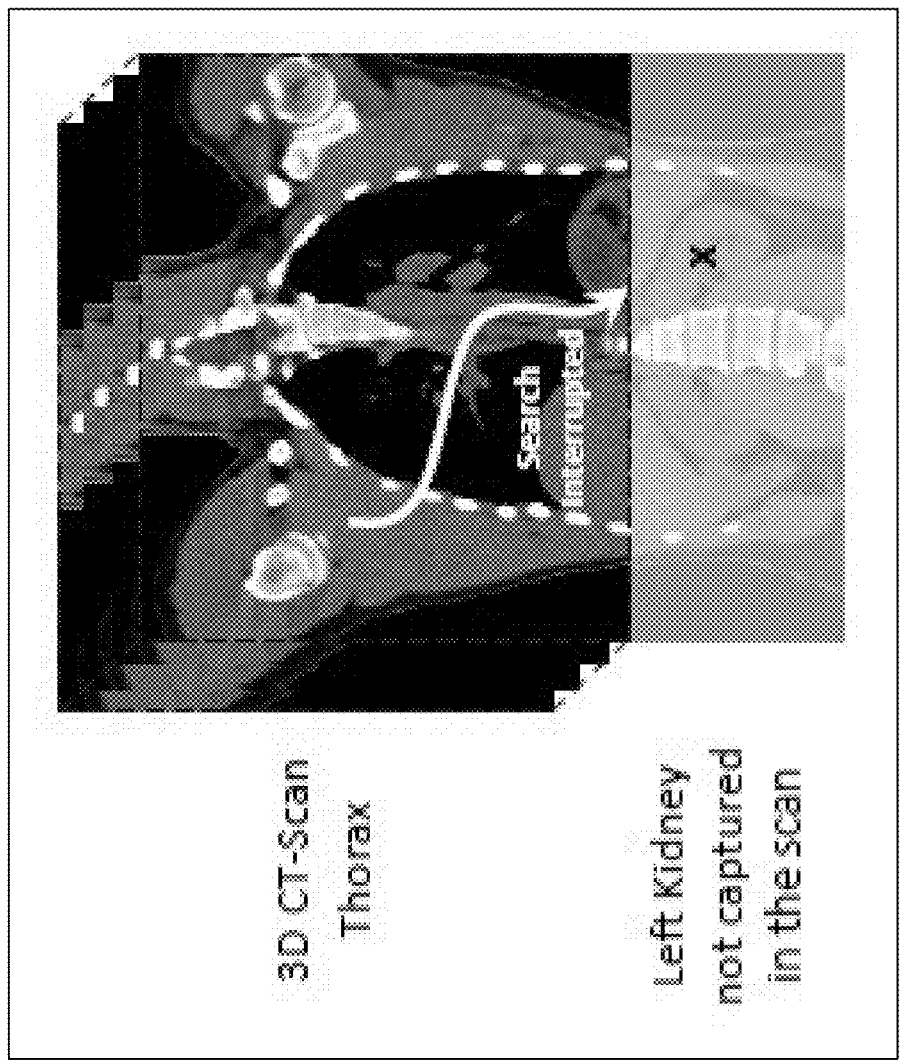
FIG. 23 illustrates an artificial agent detecting the absence of a landmark according to an embodiment.

By approaching object detection as a search problem, the artificial agent may detect the absence of landmarks, such as caused by a change in field-of-view or when a particular organ is missing from the scan (e.g. if an organ is physically removed from the patient body, such as a missing kidney). Given an image I with $\vec{PGT}$ outside the image space, trajectories starting on lowest scale-level from an arbitrary point $\vec{Po}$ will reach a point on the image border and attempt to leave the image space. By training the system on differently cropped images, consistent behavior leads to a natural recognition of the absence of landmarks. FIG. 23 illustrates an example of an artificial agent detecting the absence of a landmark. A search-path for finding the left kidney in a thorax CT scan that did not capture the left kidney (e.g., marked by x). The trajectory leaves the image space, signaling the absence of the left kidney from the scan.

Intelligent multi-scale image parsing using MSDRL may be asymptotically three orders of magnitude faster than other image parsing solutions using deep learning. For example, the multiscale landmark detection time averages 37 milliseconds on full body CT scans of 150×200×500 voxels using 8 mm, 4 mm, and 2 mm resolutions during parsing. In this example, results are detected at 2 mm. Comparably, scanning using other deep learning solutions may require between 20-30 seconds on similarly sized full body CT scans with parsing entirely performed at the final resolution of 2 mm. Conversely, the system speed for detecting a left or right kidney using three scales provided an average runtime of 37 milliseconds, with a longest runtime of 87 milliseconds and a shortest runtime of 8 milliseconds.

Intelligent image parsing using multiple scales may further increase the accuracy and reliability of landmark detection. For example, Table 3 below shows the results of multi-scale image parsing obtained from a dataset including over 1400 three-dimensional CT volumes split randomly in approximately 1100 training examples and 300 test examples:

TABLE 3

| | | Mean | Median | STD | 95% | Max | Failures |
|---|---|---|---|---|---|---|---|
| Right Kidney | Top Point | 3.6 | 2.7 | 4.6 | 7.5 | 35.9 | 0.7% |
| Right Kidney | Center | 7.5 | 6.5 | 5.3 | 17.2 | 31.3 | 0.0% |
| Left Kidney | Top Point | 3.9 | 2.8 | 4.3 | 8.3 | 32.7 | 1.5% |
| Left Kidney | Center | 6.4 | 6.8 | 7.2 | 17.4 | 54.1 | 0.0% |
| Trachea | Bronchial Bif. | 4.0 | 3.4 | 3.3 | 8.8 | 18.9 | 0.0% |
| Carotid Artery | Bifurcation | 1.8 | 0.8 | 2.9 | 6.9 | 18.2 | 0.8% |

The results provided in Table 3 provide errors measured in mm. Thus, Intelligent multi-scale image parsing using MSDRL may provide the ability to reliably detect landmarks in three-dimensional medical images (e.g., CT, MR, Ultrasound, PET-CT, MR-PET, etc.) in real-time, providing for new applications for the medical images. For example, image formation may be performed in real-time inside the scanner, allowing for fast image analysis and diagnosis used in trauma scans (e.g., when time is of the essence) and during image-based guidance applications in the operating room.

Image Modalities

While the disclosed embodiments are described in the context of anatomical landmark detection, other applications of these embodiments may be used in the context of image analysis and general image understanding. For example, (simultaneous) object detection and segmentation may be applied to quantifying image analysis limitations in terms of accuracy, result confidence, policy performance, and optimization of general computational requirements. The disclosed embodiments are further applicable to a variety of action sets.

The disclosed embodiments of medical image parsing (e.g., landmark detection), training of intelligent, generic agents overcome the limitations of predefined, standard machine learning approaches. Using Q-learning based framework deep learning techniques directly approximate the optimal behavior of the agent in a trial-and-error environment, describing the underlying problem. The artificial agent of the disclosed embodiments is adaptable to different landmarks from different image modalities, such that the artificial agent is capable of automatically discovering and developing strategies for landmark detection at high accuracy while simultaneously evaluating the medical image using the strategy. These agents may extend the framework on a wide range of image analysis applications, creating agents that can solve multiple problems in an intelligent, principled way.

The disclosed embodiments are additionally robust for use with other multi-dimensionalities. For example, a goal is achieved by providing a system capable of generating an artificial agent capable of scaling execution of learning and executing image analysis of a two-dimensional dataset. A goal is further achieved providing a flexible enough artificial agent capable of learning and executing image analysis of a two-dimensional dataset as well as in three-dimensional dataset without fundamentally changing the structure of the system. Only changes in the identification data are necessary, such as establishing a landmark target location based on a three-dimensional location (e.g. a three-dimensional point or a voxel), instead of a two-dimensional target location (e.g., a two-dimensional location or a pixel). Additional actions or sets of actions, may be applicable to some applications but not others, such as three-dimensional rotation of the state space with respect to its position within a three-dimensional image. While different agents are trained for each individual target landmarks, the process generating and training the artificial agent is naturally and self-adaptive requiring no fundamental changes to establish a structure of the artificial agent's learning process and training based on a specific task or image modality.

Experience Based Adaptive Agents

The disclosed system using artificial agents may be further adaptive in some embodiments to further optimize repeated user input, workflows, or other environment or local requirements. Techniques described above with respect to self-determining optimization methods may be further employed to customize annotation behavior, repeat image quality settings, self-optimize workflows based on local environments, and interact with the user or local population of users associated with use of artificial agents or post-processing diagnosis or analysis associated with the detected anatomical landmark target. An agent may generate an annotation indicative of the determine location of the target landmark in the medical image and provide the medical image and generated annotation for display.

Adaptation based on user experience may be localized with respect to a single workstation or processor or may be aggregated from multiple similar systems. User based preferences may require identification protocols such as user id/password entry, facial recognition, biometric sensor identification or user identification protocols. Some adaptivity, such as application or task centric adaptivity, may not require individual user identification. Adaptation may be further localized based on country, hospital, type of medical profession, medical specialty or other group exhibiting similar usage characteristics.

Experience based adaptivity may include assimilation of model behavior and optimization of individual, repeated interactions with the system. These gradual personalization models may optimize personalization strategy through repeated interaction, or may prompt the user to create personalized models for individual users or patients.

User interactions may include pre-defining one or more actions in a set of actions for target state location identification. Users may select or identify an action via providing input to an imaging system 48. Users may also annotate images prior to training, following training, prior to testing, or following testing of an image. The artificial agent may learn, via methods disclosed above, example annotation actions received via user input to imaging system 48 or selection of image optimization parameters such as contrast, size, brightness or other parameter of a test image or training image.

User inputs to an imaging system 48 may be observed by the artificial agent and an optimal action-value function approximator may specify the behavior of the artificial agent based on the observed input. The user entered inputs may be replicated by the agent. The artificial agent, may suggest a next action of the processor based on the replicated user inputs.

Device and System Architecture

FIG. 13 depicts a system for generating and training an artificial agent for intelligent image parsing and evaluating medical images of a patient via the artificial agent, such as locating ventricle landmarks on a medical image scan of a patient's heart. The system includes an imaging system 48, a memory 52, an image processor 50, and a display 54. Additional, different, or fewer components may be provided. For example, a network or network connection is provided, such as for networking with a medical imaging network or data archival system. In another example, a user interface is provided.

The image processor 50, memory 52, and display 54 are part of the medical imaging system 48. Alternatively, the image processor 50, memory 52, and/or display 54 are part of an archival and/or image processing system, such as associated with a medical records database workstation or server. In other embodiments, the image processor 50, memory 52, and/or display 54 are a computer, such as desktop or laptop, a workstation, a server, a network, or combinations thereof.

The imaging system 48 is a medical diagnostic imaging system. Ultrasound, computed tomography (CT), x-ray, fluoroscopy, positron emission tomography, single photon emission computed tomography, and/or magnetic resonance (MR) systems may be used. The imaging system 48 may include a transmitter and includes a detector for scanning or receiving data representative of the interior of the patient.

In one embodiment, the imaging system 48 is a CT system. An x-ray source is connected with a gantry. A detector is also connected with the gantry opposite the x-ray source. The patient is positioned between the source and detector. The source and detector are on opposite sides of the patient and rotate about the patient. The detected x-ray energy passing through the patient is reconstructed or transformed into data representing different spatial locations within the patient.

In another embodiment, the imaging system 48 is an MR system. The MR system includes a main field magnet, such as a cryomagnet, and gradient coils. A whole-body coil is provided for transmitting and/or receiving. Local coils may be used, such as for receiving electromagnetic energy emitted by atoms in response to pulses. Other processing components may be provided, such as for planning and generating transmit pulses for the coils based on the sequence and for receiving and processing the received k-space data. The received k-space data is converted into object or image space data with Fourier processing.

The memory 52 may be a graphics processing memory, a video random access memory, a random access memory, system memory, cache memory, hard drive, optical media, magnetic media, flash drive, buffer, database, combinations thereof, or other now known or later developed memory device for storing image data, artificial agents, and/or data and programs for generating and/or training an artificial agent. The memory 52 is part of the imaging system 48, part of a computer associated with the processor 50, part of a database, part of another system, a picture archival memory, or a standalone device.

The memory 52 or other memory is alternatively or additionally a non-transitory computer readable storage medium storing data representing instructions executable by the programmed processor 50 for generating and training an artificial agent for intelligent image parsing and evaluating medical images of a patient via the artificial agent. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 50 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for generating and training an artificial agent for intelligent image parsing and evaluating medical images of a patient via the artificial agent. The image processor 50 is a single device or multiple devices operating in serial, parallel, or separately. The image processor 50 may be a main processor of a computer, such as a laptop or desktop computer, or may be a processor for handling some tasks in a larger system, such as in an imaging system. The image processor 50 is configured by instructions, design, hardware, and/or software to perform the acts discussed herein.

The image processor 50 is configured to implement the acts of the preceding figures. For example, the image processor 50 is configured to generate an artificial agent for intelligent image parsing as in accordance with the method of FIGS. 9-11. The image processor 50 may be alternatively or additionally configured to implement training of the artificial agent is illustrated in FIG. 12.

As of the solution, the image processor 50 interacts with the medical imaging system 48 or other source of scan data, stores data in different parts of the memory 52, and generates output to assist in medical diagnosis and/or therapy. Manual segmentation is highly inefficient, not cost effective, and uses different processes than the technical solution.

The display 54 is a monitor, LCD, projector, plasma display, CRT, printer, or other now known or later developed devise for outputting visual information. The display 54 receives images, graphics, text, quantities, or other information from the processor 50, memory 52, or imaging system 48. One or more medical images are displayed. The images are of a region of the patient, such as images of the heart. The image includes an indication, such as a graphic or colorization, of the boundary or other segmentation. Alternatively, or additionally, the image includes a quantity based on the boundary. The quantity may be displayed as the image without the medical image representation of the patient.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for intelligent multi-scale medical image parsing, the method comprising:
    determining, by a processor, a set of actions comprising parametric actions comprising movements in each direction that an artificial agent may select from a set of upward, downward, left, right, forward and backwards movements in a parametric space with respect to a training medical image;
    determining, by the processor, scale actions specifying navigation from coarse to fine in a scale space with respect to the training medical image;
    establishing, by the processor, a reward system based on applying each action of the set of actions and based on at least one target location of the training medical image; and
    learning, by the processor, behavior of the artificial agent to maximize a cumulative future reward value of the reward system by navigating a state space of discrete portions of the training image, wherein the behavior of the artificial agent is a sequence of actions from the set of actions navigating the artificial agent towards the at least one target location of the training medical image until convergence, performing a scale action on the state space, and at a different resolution navigating the artificial agent towards the at least one target location until convergence.

2. The method of claim 1, further comprising:
    applying, by the processor, the learned artificial agent on a test image to automatically parse image content for a landmark location; and
    displaying the identified landmark location in the test image.

3. The method of claim 2, wherein applying the learned artificial agent comprises determining a next action of the artificial agent based on balancing maximization of the cumulative future reward value by actions changing the parametric space and by actions changing the scale space.

4. The method of claim 1, wherein the at least one target location is an anatomical landmark location, and wherein the target location is defined by a position parameters of the landmark anatomical landmark, and wherein a reward value is indicative of a proximity to the at least one target location.

5. The method of claim 1, wherein learning the behavior of an artificial agent further comprises:
    generating an experience memory database including a predefined number of last evaluated parametric spaces and scale spaces for the training medical image;
    sampling the experience memory database; and
    updating parameters of the artificial agent based on the experience memory database.

6. The method of claim 1, wherein learning the behavior of the artificial agent further comprises:
    parameterizing the behavior of the artificial agent using a deep neural network; and optimizing the behavior of the artificial agent using an episodic trajectory for the training medical image based on discrete portions of the training medical image via the parametric space and scale space, wherein the episodic trajectory is indicative of a series actions of the set of actions of the artificial agent.

7. The method of claim 1, wherein the scale actions change the scale space of the state space by increasing or decreasing a resolution with respect to the training medical image.

8. The method of claim 7, wherein the set of actions further includes an action in which the parametric space is unchanged.

9. A system for training an artificial agent for intelligent multi-scale medical image parsing, the system comprising:
    at least one processor; and
    at least one memory including computer program code for one or more programs, the at least one memory and the computer program code configured to, with the at least one processor, cause the system to:
    receive a plurality of training medical images;
    train, based on the plurality of training medical images, an artificial agent to parse a test image to identify a landmark location in the test image, wherein training the artificial agent comprises training a search strategy model to search for the landmark location by parsing the test image by performing a series of actions, the series of actions comprising a set of upward, downward, left, right, forward and backwards movements in a patch of the test image that navigate the artificial agent towards the landmark location, changing a scale of the patch of the test image to parse the test image by searching less than an entire test image, and performing a second series of actions comprising the set of upward, downward, left, right, forward and backwards movements; and
    store the trained artificial agent for automatically parsing test image data to identify the landmark location in the test image.

10. The system of claim 9, wherein searching for the landmark location comprises changing the position of the patch at a first scale, changing the scale from the first scale to a second scale, and changing the position of the patch at the second scale.

11. The system of claim 9, wherein training the search strategy model comprises encoding parameters of search strategy model in a multilayer data representation.

12. The system of claim 11, wherein the multilayer data representation is a deep neural network.

13. The system of claim 12, wherein training the artificial agent comprises using experience memory from previously parsed patches at different scales to solve for parameters of the deep neural network.

14. The system of claim 9, wherein training the search strategy model comprises maximizing a future reward using a reward system based on reward values for each position and scale change of the patch.

15. A method for intelligent multi-scale landmark identification in a medical image, the method comprising:

parameterizing a patch of the medical image in a trained hierarchical data representation, the hierarchical data representation trained to navigate an artificial agent towards a landmark location by maximizing a future reward of a reward system for each of a plurality of available actions that reposition the patch in an upward, downward, left or right direction in the medical image;

rescaling the patch to a higher or lower resolution;

repeating the training of the hierarchical data representation to navigate the artificial agent towards the landmark location in the rescaled patch;

identifying the landmark location in the rescaled patch of the medical image; and displaying the medical image with an annotation indicative of the identified landmark location.

16. The method of claim 15, wherein identifying the landmark location comprises performing a sequence of actions to move a location of the patch toward a location of a target patch and to increase the resolution of the patch, the target patch including the landmark location in the medical image.

17. The method of claim 16, wherein the sequence of actions comprises a path converging on the landmark location by parsing less than an entire medical image.

18. The method of claim 17, wherein determining the sequence of actions comprises parameterizing at least one previous patch in the hierarchical data representation after repositioning and rescaling the patch.

19. The method of claim 18, wherein the hierarchical data representation is a deep neural network.

* * * * *